US009310376B2

(12) United States Patent
Cao et al.

(10) Patent No.: US 9,310,376 B2
(45) Date of Patent: *Apr. 12, 2016

(54) METHODS OF MACROMOLECULAR ANALYSIS USING NANOCHANNEL ARRAYS

(71) Applicant: BioNano Genomics, Inc., San Diego, CA (US)

(72) Inventors: Han Cao, San Diego, CA (US); Parikshit A Deshpande, Princeton, NJ (US); Michael D Austin, San Diego, CA (US); Michael Boyce-Jacino, Titusville, NJ (US)

(73) Assignee: BIONANO GENOMICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/195,474

(22) Filed: Mar. 3, 2014

(65) Prior Publication Data

US 2014/0249039 A1 Sep. 4, 2014

Related U.S. Application Data

(63) Continuation of application No. 12/057,987, filed on Mar. 28, 2008, now Pat. No. 8,722,327.

(60) Provisional application No. 60/908,582, filed on Mar. 28, 2007, provisional application No. 60/908,584, filed on Mar. 28, 2007.

(51) Int. Cl.
*C12Q 1/68* (2006.01)
*C12M 1/34* (2006.01)
*C07H 21/02* (2006.01)
*C07H 21/04* (2006.01)
*G01N 33/58* (2006.01)
*B01L 3/00* (2006.01)
*G01N 21/64* (2006.01)

(52) U.S. Cl.
CPC ........ *G01N 33/582* (2013.01); *B01L 3/502761* (2013.01); *G01N 21/645* (2013.01); *G01N 21/6428* (2013.01); *B01L 2200/0663* (2013.01); *B01L 2200/0668* (2013.01); *B01L 2200/12* (2013.01); *B01L 2300/041* (2013.01); *B01L 2300/0654* (2013.01); *B01L 2300/089* (2013.01); *B01L 2300/0816* (2013.01); *B01L 2300/0864* (2013.01); *B01L 2300/0887* (2013.01); *B01L 2300/161* (2013.01); *B01L 2400/0406* (2013.01); *B01L 2400/0415* (2013.01); *B01L 2400/0487* (2013.01); *B01L 2400/086* (2013.01); *C12Q 2563/107* (2013.01)

(58) Field of Classification Search
USPC ............. 435/6.1, 6.11, 287.2; 536/23.1, 24.3; 977/704
See application file for complete search history.

(56) References Cited

U.S. PATENT DOCUMENTS

| 5,079,169 | A | 1/1992 | Chu et al. |
|---|---|---|---|
| 5,314,829 | A | 5/1994 | Coles |
| 5,356,776 | A | 10/1994 | Kambara et al. |
| 5,405,519 | A | 4/1995 | Schwartz |
| 5,427,663 | A | 6/1995 | Austin et al. |
| 5,599,664 | A | 2/1997 | Schwartz |
| 5,637,458 | A | 6/1997 | Frankel et al. |
| 5,720,928 | A | 2/1998 | Schwartz |
| 5,837,115 | A | 11/1998 | Austin et al. |
| 5,867,266 | A | 2/1999 | Craighead |
| 6,117,634 | A | 9/2000 | Langmore |
| 6,147,198 | A | 11/2000 | Schwartz |
| 6,150,089 | A | 11/2000 | Schwartz |
| 6,174,671 | B1 | 1/2001 | Anantharaman et al. |
| 6,197,557 | B1 | 3/2001 | Makarov et al. |
| 6,210,896 | B1 | 4/2001 | Chan et al. |
| 6,214,246 | B1 | 4/2001 | Craighead |
| 6,221,592 | B1 | 4/2001 | Schwartz et al. |
| 6,263,286 | B1 | 7/2001 | Gilmanshin et al. |
| 6,340,567 | B1 | 1/2002 | Schwartz et al. |
| 6,344,319 | B1 | 2/2002 | Bensimon et al. |
| 6,355,420 | B1 | 3/2002 | Chan |
| 6,403,311 | B1 | 6/2002 | Arnon |
| 6,438,279 | B1 | 8/2002 | Craighead et al. |
| 6,464,842 | B1 | 10/2002 | Golovchenko et al. |
| 6,607,888 | B2 | 8/2003 | Schwartz et al. |
| 6,627,067 | B1 | 9/2003 | Branton et al. |
| 6,635,163 | B1 | 10/2003 | Han et al. |
| 6,696,022 | B1 | 2/2004 | Chan et al. |

(Continued)

FOREIGN PATENT DOCUMENTS

| CN | 1379857 A | 11/2002 |
|---|---|---|
| EP | 0497272 A1 | 8/1992 |

(Continued)

OTHER PUBLICATIONS

Slater, et al., "Bidirectional Transport of Polyelectrolytes Using Self-Modulating Entropic Ratchets," Physical Review Letters, The American Physical Society, 78(6), Feb. 1997, 1170-1173.
Office Action dated Sep. 29, 2014 issued in Canadian Patent Application No. 2682275.
Office Action dated Nov. 14, 2014 issued in Chinese Patent Application No. 201310189106.6.
Cao et al., "Fabrication of 10 nm enclosed nanofluidic channels," Applied Physics Letters, 81(1):174-176 (2002).

(Continued)

*Primary Examiner* — Narayan Bhat
(74) *Attorney, Agent, or Firm* — Knobbe, Martens, Olson & Bear, LLP

(57) ABSTRACT

Methods of analyzing features such as the physical size of macromolecules or biomarkers along large genomic DNA molecules were disclosed as wen as the devices for carrying out such high throughput analysis in a massively parallel fashion. Methods of fabricating such devices are also disclosed.

27 Claims, 19 Drawing Sheets

(56) References Cited

U.S. PATENT DOCUMENTS

| | | | |
|---|---|---|---|
| 6,753,200 B2 | 6/2004 | Craighead et al. |
| 6,762,059 B2 | 7/2004 | Chan et al. |
| 6,772,070 B2 | 8/2004 | Gilmanshin et al. |
| 6,790,671 B1 | 9/2004 | Austin |
| 6,927,065 B2 | 8/2005 | Chan et al. |
| 7,217,562 B2 | 5/2007 | Cao et al. |
| 7,262,859 B2 | 8/2007 | Larson et al. |
| 7,282,330 B2 | 10/2007 | Zhao et al. |
| 7,312,033 B2 | 12/2007 | Accola et al. |
| 7,316,769 B2 | 1/2008 | Craighead et al. |
| 7,351,538 B2 | 4/2008 | Fuchs et al. |
| 7,371,520 B2 | 5/2008 | Zhao et al. |
| 7,402,422 B2 | 7/2008 | Fuchs et al. |
| 7,427,343 B2 | 9/2008 | Han et al. |
| 7,670,770 B2 | 3/2010 | Chou et al. |
| 7,771,944 B2 | 8/2010 | Xiao et al. |
| 7,775,368 B2 | 8/2010 | Schwartz et al. |
| 7,831,392 B2 | 11/2010 | Marco et al. |
| 7,833,398 B2 | 11/2010 | Craighead et al. |
| 7,918,979 B2 | 4/2011 | Han et al. |
| 7,960,105 B2 | 6/2011 | Schwartz et al. |
| 8,137,569 B2 | 3/2012 | Harnack et al. |
| 8,168,380 B2 | 5/2012 | Chan et al. |
| 8,628,919 B2 | 1/2014 | Xiao et al. |
| 8,663,780 B2 | 3/2014 | Harnack et al. |
| 8,722,327 B2 | 5/2014 | Cao et al. |
| 2001/0055764 A1 | 12/2001 | Empedocles et al. |
| 2002/0110818 A1 | 8/2002 | Chan |
| 2002/0119455 A1 | 8/2002 | Chan |
| 2002/0123063 A1 | 9/2002 | Gjerde et al. |
| 2002/0197639 A1 | 12/2002 | Shia et al. |
| 2003/0059822 A1 | 3/2003 | Chan et al. |
| 2003/0066749 A1 | 4/2003 | Golovchenko et al. |
| 2003/0104428 A1 | 6/2003 | Branton et al. |
| 2003/0162181 A1 | 8/2003 | Yang et al. |
| 2003/0209314 A1 | 11/2003 | Guo et al. |
| 2003/0219792 A1 | 11/2003 | Armes et al. |
| 2003/0219805 A1 | 11/2003 | Kelman et al. |
| 2003/0232346 A1 | 12/2003 | Su |
| 2003/0235854 A1 | 12/2003 | Chan et al. |
| 2004/0009612 A1 | 1/2004 | Zhao et al. |
| 2004/0033515 A1 | 2/2004 | Cao et al. |
| 2004/0166025 A1 | 8/2004 | Chan |
| 2004/0195098 A1 | 10/2004 | Broadley et al. |
| 2004/0197843 A1 | 10/2004 | Chou et al. |
| 2005/0028538 A1 | 2/2005 | Kurn et al. |
| 2005/0082204 A1 | 4/2005 | Schwartz et al. |
| 2005/0208538 A1 | 9/2005 | Kurn et al. |
| 2005/0234656 A1 | 10/2005 | Schwartz et al. |
| 2005/0250117 A1 | 11/2005 | Su et al. |
| 2006/0011862 A1 | 1/2006 | Bernstein |
| 2006/0068440 A1 | 3/2006 | Chan et al. |
| 2006/0088944 A1 | 4/2006 | Schwartz et al. |
| 2006/0199202 A1 | 9/2006 | Lyamichev et al. |
| 2006/0275806 A1 | 12/2006 | Schwartz et al. |
| 2006/0275911 A1 | 12/2006 | Wang et al. |
| 2007/0128083 A1 | 6/2007 | Yantz |
| 2007/0161028 A1 | 7/2007 | Schwartz et al. |
| 2007/0219367 A1 | 9/2007 | Shchepinov et al. |
| 2008/0003689 A1 | 1/2008 | Lee |
| 2008/0085552 A1 | 4/2008 | Larson et al. |
| 2008/0103296 A1 | 5/2008 | Zhao |
| 2008/0242556 A1 | 10/2008 | Cao et al. |
| 2008/0254549 A1 | 10/2008 | Fuchs |
| 2009/0076735 A1 | 3/2009 | Briska et al. |
| 2009/0104611 A1 | 4/2009 | Schwartz et al. |
| 2009/0208950 A1 | 8/2009 | Briska |
| 2009/0317804 A1 | 12/2009 | Briska |
| 2010/0028886 A1 | 2/2010 | Briska |
| 2011/0171634 A1 | 7/2011 | Xiao |
| 2011/0171741 A1 | 7/2011 | Wang et al. |
| 2011/0210272 A1 | 9/2011 | Chan et al. |
| 2011/0306504 A1 | 12/2011 | Xiao et al. |
| 2012/0196382 A1 | 8/2012 | Chan et al. |
| 2012/0217161 A1 | 8/2012 | Chan et al. |
| 2012/0237936 A1 | 9/2012 | Xiao et al. |
| 2013/0177902 A1 | 7/2013 | Xiao et al. |
| 2013/0240357 A1 | 9/2013 | Xiao et al. |
| 2014/0030705 A1 | 1/2014 | Deshpande et al. |
| 2014/0221218 A1 | 8/2014 | Han et al. |
| 2014/0249039 A1 | 9/2014 | Han et al. |

FOREIGN PATENT DOCUMENTS

| | | |
|---|---|---|
| JP | 2003-507026 | 2/2003 |
| JP | 2004-147658 | 5/2004 |
| JP | 2005-505754 | 2/2005 |
| JP | 2005-518215 | 6/2005 |
| JP | 2005-524413 | 8/2005 |
| JP | 2005-532822 | 11/2005 |
| JP | 2005-533636 | 11/2005 |
| JP | 2006-521786 | 9/2006 |
| WO | WO 98/39485 | 9/1997 |
| WO | WO 98/35012 | 8/1998 |
| WO | WO 00/079257 | 12/2000 |
| WO | WO 01/13088 | 2/2001 |
| WO | WO 01/13088 A | 2/2001 |
| WO | WO 02/065138 | 8/2002 |
| WO | WO 02/099398 | 12/2002 |
| WO | WO02/099398 | 12/2002 |
| WO | WO 02/101095 A1 | 12/2002 |
| WO | WO 03/010289 A2 | 2/2003 |
| WO | WO 03/072805 A2 | 9/2003 |
| WO | WO 03/106620 A2 | 12/2003 |
| WO | WO 03/106693 | 12/2003 |
| WO | WO 2005/078137 | 8/2005 |
| WO | WO2005078137 | 8/2005 |
| WO | WO 2006/102321 | 9/2006 |
| WO | WO 2007/065025 | 6/2007 |
| WO | WO 2010/002883 | 1/2010 |
| WO | WO 2010/053980 | 5/2010 |
| WO | WO 2010/059731 | 5/2010 |
| WO | WO 2011/050147 | 4/2011 |

OTHER PUBLICATIONS

Cao et al., "Gradient nanostructures for interfacing microfluidics and nanofluidics," Applied Physics Letters, AIP, American Institute of Physics, Melville, NY, vol. 81, No. 16, pp. 3058-3060 (2002).

Chinese Office Action dated Jun. 29, 2012 for Chinese Patent Application No. 200880017550.7 filed Mar. 28, 2008.

European Search Report dated May 31, 2013 for European Application No. EP 12194842.6 filed Nov. 29, 2012.

Examination Report dated Nov. 9, 2012 in Australian Application No. 2008232616 filed Mar. 28, 2008.

International Search Report and Written Opinion dated Jan. 19, 2009 for PCT Application No. PCT/US2008/058671 filed Mar. 28, 2008.

Office Action dated Sep. 25, 2012 for Japanese Application 2010-501259 filed Mar. 28, 2008.

Examination Report dated Dec. 23, 2010 for European Application No. 08744609.2 filed Mar. 28, 2008.

Examination Report dated Jul. 23, 2012 for European Application No. 08744609.2 filed Mar. 28, 2008.

Office Action dated Feb. 26, 2014 for Chinese Patent Application No. 201310189106.6 filed May 21, 2013.

European Partial Search Report dated Feb. 5, 2014 for European Application No. EP 13150068.8 filed Jan. 2, 2013.

Final Decision of Rejection dated Aug. 13, 2013 for Japanese Application 2010-501259 filed Mar. 28, 2008.

Chinese Office Action dated Nov. 14, 2012 for Chinese Patent Application No. 200880017550.7 filed Mar. 28, 2008.

European Extended Search Report dated Jun. 18, 2014 issued in European Patent Application No. 13150068.8.

Office Action dated Aug. 12, 2014 issued in Korean Patent Application No. 10-2009-7022447.

Amann R et al.: "In situ visualization of high genetic diversity in a natural microbial community", Journal of Bacteriology, American Society for Microbiology, Washington, DC; US, vol. 178, No. 12, Jun. 1, 1996, pp. 3496-3500.

Austin et al.: "Scanning the Controls: Genomics and Nanotechnogloy," IEEE Transactions on Nanotechnology 1: 12-18, 2002.

(56) References Cited

OTHER PUBLICATIONS

Cai et al.: "Ordered restriction endonuclease maps of artificial chromosomes created by optical mapping on surfaces," PNAS 92: 5164-8, 1995.
Cai et al.: "High-resolution restriction maps of bacterial artificial chromosomes constructed by optical mapping." Proc. Natl. Acad. Sci. USA, vol. 95, No. 7, pp. 3390-3395 (1998).
Castro et al.: "Single-molecule detection of specific nucleic acid sequences in unamplified genomic DNA." Analytical Chemistry, 69(19):3915-3920 (1997).
Chan et al.: "DNA mapping using microfluidic stretching and single molecule detection of fluorescent site-specific tags," Genome Research 14: 1137-1146, 2004.
Chang et al.: "DNA-Mediated Fluctuations in Ionic Current through Silicon Oxide Nanopore Channels," Nano Letters 4: 1551-1556, 2004.
Chen et al.: "Atomic Layer Deposition to Fine-Tune the surface Properties and Diameters of Fabricated Nanopores," Nano Letters 4: 1333-1337, 2004.
Chen et al.: "Probing Single DNA Molecule Transport Using Fabricated Nanopores," Nano Letters 4: 2293-2298, 2004.
Chinese Office Action dated Mar. 13, 2013 for Chinese Patent Application No. 200980154567.1.
Chinese Office Action dated Nov. 21, 2013 for Chinese Patent Application No. 200980154567.1.
Chou et al.: "A Microfabricated Device for Sizing and Sorting DNA Molecules," Proc. Natl. Acad. Sci. USA, Jan. 1999, 96, 11-13.
Conrad et al.: "A high-resolution survey of deletion polymorphism in the human genome," Nature Genetics 38: 75-81, 2006.
Czaplewski et al.: "Nanofluidic channels with elliptical cross sections formed using a nonlithographic process," Applied Physics Letters, Dec. 8, 2003, 83(23), 836-4838.
Deamer et al.: "Characterization of Nucleic Acids by Nanopore Analysis," Acc Chem Res 35: 817-825, 2002.
Deegan et al.: "Contact line deposits in an evaporating drop," Physical Review E, Jul. 2000, 62(1), 756-765.
Dietrich et al.: "Advances in the Development of a Novel Method to be used in Proteomics using Gold Nanobeads," U/trasens/tive and Single-Molecule etection Technologies, edited by Jorg Enderlein, et al, Proc. of SPIE vol. 6092, 6092C (2006).
Eichler: "Widening the spectrum of human genetic variation," Nature Genetics 38: 9-11, 2006.
European Office Action dated Aug. 14, 2012 for European Patent Application No. 09760398,9.
European Office Action dated Oct. 18, 2013 for European patent application No. 09774334,8.
Extended European Search Report dated Oct. 22, 2013 for European patent application No. 13179160.0.
FDA Redbook 2000 Genotoxicity Tests, available at www.cfsan.fda.gov.
Fu et al.: "Sequencing Double-Stranded DNA by Strand Displacement", Nucleic Acids Research, Information Retrieval Ltd., vol. 25, No. 3, (Jan. 1997), pp. 677-679.
Gad et al.: "Bar code screening on combed DNA for large rearragements of the BRCA1 and BRCA2 genes in French breast cancerfamilies." J Med Genet 39: 17-21, 2002.
Gad et al.: "Color bar coding the BRCA1 gene on combed DNA: A useful strategy for detecting large gene arrangements." Genes, Chromosomes and Cancer 31: 5-84, 2001.
Gracheva et al.: "Simulation of the electric response of DNA translocation through a semiconductor nanopore-capacitor," Nanotechnology 17: 622-633, 2006.
Guidance for industry S2B Genotoxicity: A standard Battery for Genotoxicity Testing of Pharmaceuticals, Jul. 1997, ICH.
Guo et al: "Fabrication of Size-Controllable Nanofluidic Channels by Nanoimprinting and its Application for DNA Stretching", 2004, 4, 69-73.
Hashioka et al.: "Simple and Quick Detection of Target DNA by Hybridization in Nano Gap Channel Array." 9th International Conference on Miniaturized Systems or Chemistry and Life Sciences, vol. 1, pp. 730-732 (2005).
Henriquez et al.: "The resurgence of Coulter counting for analyzing nanoscale objects," The Analyst, 2004, 129, 478-482.
Hinds et al.: "Common deletions and SNPs are in linkage disequilibrium in the human genome," Nature Genetics 38: 82-85, 2006.
Howorka et al.: "Kinetics of duplex formation for individual DNA strands within a single protein nanopore," PNAS 98: 12996-13001, 2001.
Howorka et al.: "Sequence-specific detection of individual DNA strands using engineered nanopores," Nature Biotechnology 19: 636-639, 2001.
International Preliminary Report on Patentability dated Feb. 23, 2009 for PCT Application No. PCT/US2007/016408.
International Search Report and Written Opinion dated Sep. 10, 2010 for PCT Application No. PCT/US2009/049244.
International Search Report dated Apr. 7, 2011 for PCT Application No. PCT/US2010/053513 filed Oct. 21, 2010.
International Search Report dated Aug. 16, 2010 for PCT Application No. PCT/US2009/064996.
International Search Report dated Aug. 17, 2012 for Application PCT/US2011/057115.
Japanese Office Action dated Jul. 24, 2012 for Japanese Patent Application No. 2009-520847 (English translation thereof is enclosed).
Jo et al.: "A single-molecule barcoding system using nanoslits for DNA analysis." Proc. Natl. Acad. Sci., 104(8):2673-2678 (2007).
Johansson et al.: "Primary vs. secondary neoplasia-associated chromosomal abnormalities-balanced rearrangements vs genomic imbalances?" Genes, Chromosomes and Cancer 16: 155-163, 1996.
Kasianowicz et al.: "Characterization of individual polynucleotide molecules using a membrane channel," PNAS 93: 13770-13773, 1996.
Koppal et al.: "Spanning the Drug Pipeline," Drug Discovery & Development; Sep. 13, 2005, 1 page, http://www.dddmag.com.
Kuhn et al., "Labeling of unique sequences in double-stranded DNA at sites of vicinal nicks generated by nicking endonucleases." Nucleic Acids Research, 36(7):e40:1-10 (2008).
Li et al.: "Ion-beam sculpting at nanometer length scales," Nature 412: 166-169, 2001.
Li et al.: "DNA molecules and configurations in a solid-state nanopore microscope," Nature Materials 2: 611-615, 2003.
Li, et al.: "Sacrificial polymers for nanofluid channels in biological applications," Nanotechnology, 2003, 14, 578-583.
Mannion et al., Conformational Analysis of Single DNA Molecule Undergoing Entropically Induced Motion in Nanochannels, Biophysical Journal, Jun. 2006, vol. 90, pp. 4538-4545.
McCarroll et al.: "Common deletion polymorphisms in the human genome," Nature Genetics 38: 86-92, 2006.
McGee et al.: "New in Vitro, Modeling Tools May Cut Tox Attrition," Drug Discovery & Development, Aug. 4, 2005, 4 pages, http://wvvw.dddmag.com.
McGee, et al.: "Small-Animal Models Advance in Vivo ADME-Tox", Drug Discovery & Development, Jul. 5, 2005, 3 pages, http://wvvw.dddmag.com.
Meller et al.: "Rapid nanopore discrimination between single polynucleotide molecules," PNAS 97: 1079-1084, 2001.
Meller et al.: "Voltage-Driven DNA Translocations through a Nanopore," Physical Review Letters 86: 3435-3438, 2001.
Meng et al.: "Optical mapping of lambda bacteriophage clones using restriction endonucleases," Nat Genet 9: 432-438, 1995.
Mijatovic et al., "Technologies for nanoflui di csystems: top-down vs. bottom-up—a review," Lab on a Chip, Royal Society of Chemistry, Cambridge, GB, Jan. 2005, vol. 5, 492-500.
Molecular Devices website, product page for Axopatch 200B: NO date present NB/http://wvvw.moleculardevices.com/pages/instruments/cn_axopatch200b.html.
Nagata et al.: "Degradation of chromosomal DNA during apoptosis," Cell Death and Differentiation 10: 108-116, 2003.
Nath et al.: "A System for Micro/Nano Fluidic Flow", Diagnostics, 2005, Biomedical Microdevices, 7, 169-177.

(56) References Cited

OTHER PUBLICATIONS

Notice of Allowance dated Dec. 11, 2013 for Canadian Patent Application No. 2658122.
Notice of Allowance dated Jan. 23, 2014 for Australian Patent Application No. 2007338862.
Notice of Allowance dated Sep. 18, 2013 in U.S. Appl. No. 13/001,697.
Office Action dated Aug. 28, 2014 issued in European Patent Application No. 09774334.8.
Office Action dated Dec. 9, 2013 for Japanese Patent Application No. 2009-520847.
Office Action dated Feb. 10, 2015 for Australian Patent Application No. AU2009267086.
Office Action dated Feb. 24, 2014 for Chinese Patent Application No. 200980125335.3.
Office Action dated Feb. 5, 2013 for Japanese Patent Application No. 2009-520847.
Office Action dated Jan. 14, 2014 for Japanese Patent Application No. 2011-516813 dated Jan. 14, 2014.
Office Action dated Oct. 14, 2014 for Japanese Patent Application No. 2011-516813 dated Oct. 14, 2014.
Office Action dated Jan. 4, 2012 for Chinese Patent Application No. 200780034694.9.
Office Action dated Jan. 7, 2015 for Australian Patent Application No. 2011316989.
Office Action dated Mar. 25, 2014 in Chinese Patent Application No. 201310054745.1.
Office Action dated Dec. 18, 2014 in Chinese Patent Application No. 201180060380.2.
Office Action dated Mar. 28, 2013 for Canadian Patent Application No. 2658122.
Office Action dated May 13, 2014 for Japanese Patent Application No. 2011-537585.
Office Action dated May 9, 2012 for Australian Patent Application No. 2007338862.
Office Action dated May 9, 2012 of U.S. Appl. No. 13/001,697.
Office Action dated Nov. 5, 2012 for Chinese Patent Application No. 200780034694.9.
Office Action dated Jan. 20, 2015 for Japanese Patent Application No. 2013-258107.
Office Action in U.S. Appl. No. 13/710,180, mailed Mar. 14, 2014.
Office Action in U.S. Appl. No. 13/880,365, mailed Dec. 8, 2014.
Office Action dated Jan. 30, 2015 for Korean patent application No. 10-2011-7000192.
Office Action dated Apr. 15, 2015 for Canadian Patent Application No. 2682275.
Olivier et al., "High-throughput genotyping of single nucleotide polymorphisms using new biplex invader technology." Nucleic Acids Research, vol. 30, No. 12, p. E53 (2002).
Phillips et al., "Application of single molecule technology to rapidly map long DNA and study the conformation of stretched DNA." Nucleic Acids Research, 33(18):5829-5837 (2005).
Piepenburg et al., "DNA detection using recombination proteins." PLOS Biology, vol. 4, No. 7, e204 (2006).
Purves et al.: "Genotoxicity testing: Current Practices and Strategies Used by the Pharmaceutical Industry," Mutagenesis, 1995, vol. 10 No. 4 pp. 297-312.
Reccius et al.: "Compression and Free Expansion of Single DNA Molecules in Nanochannels," Phys. Rev. Letts., Dec. 21, 2005, 95, 268101-1-268101-4.
Reil et al.: "Clinical validation of a new triplex real-time polymerase chain reaction assay for the detection and discrimination of Herpes simplex virus types 1 and 2", The Journal of Molecular Diagnostics: Jul. 2008, vol. 10, No. 4, pp. 361-367.
Turner, et al.: "Monolithic nanofluid sieving structures for DNA manipulation", Journal of Vacuum Science and Technology, 16, 3835, 1998.

Storm et al.: "Fabrication of solid-state nanopores with single-nanometer precision," Nature Materials 2: 537-540, 2003.
Storm et al.: "Fast DNA Translocation through a Solid-State Nanopore," Nano Letters 5: 1193-1197, 2005.
Technology Research News, LLC, "Melted fibers make nano channels," Jan. 14, 2004, Retrieved from the internet at URL <http://wvvw.trnmag.com/Stories/2004/011404/Melted_fibers_make_nano_channels_Brief.
Tegenfeldt et al., "From the Cover: The dynamics of genomic-length DNA molecules in 100-nm channels." Proc. Natl. Acad. Sci. USA, 101(30):10979-83 (2004).
Tegenfeldt et al.: "Micro and nanofluidics for DNA analysis," Anal Bioanal Chem 378: 1678-1692, 2004.
Tegenfeldt et al.: "The dynamics of genomic-length DNA molecules in 100-nm channels," PNAS 101: 10979-10983, 2004b.
Vaandrager et al,: "DNA fiber fluorescence in situ hybridization analysis of immunoglobulin class switching in B-cell neoplasia: aberrant CH gene arrangements in follicle center-cell lymphoma", BLOOD, Oct. 15, 1998, vol. 92, No. 8, pp. 2871-2878.
Volkmuth, W., M. C. Wu, and R. H. Austin. "Observation of Electrophoresis of Single DNA-Molecules in Nanofabricated Arrays." Faseb Journal 6, No. 1 (1992): A223.
Volkmuth et al.: "DNA electrophoresis in microlithographic arrays", Department of Physics, Princeton University, Nature, vol. 358, Aug. 13, 1992, pp. 600-602.
Wade et al.: "The Quest for the $1,000 Human Genome" The New York Times, Jul. 18, 2006.
Wong et al.: "Deformation of DNA molecules by hydrodynamic focusing," J Fluid Mechanics 497: 55-65, 2003.
Written Opinion and Search Report of Intellectual Property Office of Singapore dated Jan. 9, 2013 for Singapore Patent Application No. 201009665-0.
Written Opinion dated Apr. 21, 2011 for PCT Application No. PCT/US2010/053513.
Xiao et al., "Rapid DNA mapping by fluorescent single molecule detection." Nucleic Acids Research, 35(e16):1-12 (2007).
Office Action dated Nov. 6, 2014 in U.S. Appl. No. 13/765,353.
Office Action dated Apr. 21, 2015 in U.S. Appl. No. 13/765,353.
Das et al.: "Single molecule linear analysis of DNA in nano-channel labeled with sequence specific fluorescent probes", Nucleic Acids Research, 2010, vol. 38, o. 18, 8 pages.
Second Office Action dated Dec. 9, 2014 in Chinese Patent Application No. 201310054745.1.
Office Action dated Jul. 7, 2015 in Japanese patent application No. 2014-089510.
Office Action dated May 29, 2015 for Chinese Patent Application No. 201310189106.6.
European Search Report dated May 31, 2013 for European Application No. EP 12194842.6.
Patent Examination Report No. 1 dated Feb. 10, 2015 in Australian patent application No. 2009267086.
Office action dated Aug. 20, 2015 in U.S. Appl. No. 13/765,353.
Office Action dated Sep. 17, 2014 for Chinese Patent Application No. 200980125335.3.
Office Action dated Apr. 3, 2015 for Chinese Patent Application No. 200980125335.3.
Office Action dated Oct. 25, 2013, in U.S. Appl. No. 13/129,634.
Office Action dated Jun. 6, 2014, in U.S. Appl. No. 13/129,634.
Office Action dated Jan. 2, 2015 in U.S. Appl. No. 13/129,634.
Patent Examination Report No. 1 dated Aug. 21, 2015 in Australian patent application No. 2009316628.
Second Office Action dated Sep. 11, 2015 in Chinese Patent Application No. 201180060380.2.
Examination Report dated Jun. 24, 2015 in European patent application No. 11777008.1.
Office Action in U.S. Appl. No. 13/880,365, dated May 4, 2015.
Notification on Non-Compliance with the Unity of Invention Requirement dated Sep. 7, 2015 in Russian patent application No. 2013117936.
Office Action dated Jul. 14, 2015 in U.S. Appl. No. 13/710,180.
Official Action dated Dec. 22, 2014 in Russian patent application No. 2012116604.

Signal intensity of Fluorescence signal collected from slit
(arbitrary units)

US 9,310,376 B2

METHODS OF MACROMOLECULAR ANALYSIS USING NANOCHANNEL ARRAYS

CROSS-REFERENCE TO RELATED APPLICATIONS

The present application is a continuation of U.S. patent application Ser. No. 12/057,987, filed Mar. 28, 2008, now U.S. Pat. No. 8,772,327, which claims the benefit of U.S. Application No. 60/908,582, and U.S. Application No. 60/908,584, filed on Mar. 28, 2007, the entireties of which are incorporated herein by reference.

STATEMENT OF GOVERNMENT RIGHTS

This invention was made with U.S. Government support. The Government may have certain rights in the invention under National Institutes of Health grant 1R43HG004199-01.

FIELD OF THE INVENTION

The field of the invention includes nanoscale devices, and methods of making and using such devices, for macromolecular analysis. The field of the invention also includes polynucleic acid sizing and structural analysis.

BACKGROUND OF THE INVENTION

Various scientific and patent publications are referred to herein. Each is incorporated by reference in its entirety.

Biomolecules such as DNA or RNA are long molecules composed of nucleotides, whose linear sequencing is directly related to the genomic and post-genomic expression information of the organism.

Biomolecules such as DNA or RNA are long molecules composed of nucleotides, whose linear sequencing is directly related to the genomic and post-genomic expression information of the organism.

In many cases, the mutation or rearrangement of the nucleotide sequences during an individual's life span leads to disease states such as genetic abnormalities or cell malignancy. In other cases, the small amount of sequence differences among each individual reflects the diversity of the genetic makeup of the population. Because of this, different people have different disease predisposition or respond differently to environmental stimuli and signals such as stress or drug treatments. As an example, some patients experience a positive response to certain compounds while others experience no effects or even adverse side effects. Another area of interest is the response of biomolecules such as DNA to environmental toxins or other toxic stimuli such as radiation. Toxic stimuli can lead to programmed cell death (apoptosis), a process that removes toxic or non-functioning cells. Apoptosis is characterized by morphological changes of cells and nuclei and is often accompanied by the degradation of chromosomal DNA.

Areas of population genomics, comparative/evolution genomics, medical genomics, environmental or toxicogenomics, and pharmacogenomics studying genetic diversity and medical pharmacological implications require extensive sequencing coverage and large sample numbers. Knowledge generated from such study would thus be especially valuable to the health care and pharmaceutical industry. Cancer genomics and diagnostics in particular study genomic instability events leading to tumorigenesis. All these fields would thus benefit from technologies enabling fast determination of the linear sequence, structural pattern changes of elements/regions of interests on biopolymer molecules such as nucleic acids, or epigenetic biomarkers such as methylation patterns along the biopolymers.

Most genome or epigenome analysis technologies remain too tedious or expensive for general analysis of large genomic regions or for a large population. Thus, to achieve the goal of reducing the genomic analysis cost by at least four orders of magnitude, the so-called "$1000 genome" milestone, new paradigm shift technologies enabling direct molecular analysis methods are desirable. See "The Quest for the $1,000 Human Genome", by Nicholas Wade, *The New York Times*, Jul. 18, 2006.

Additionally, it takes on average 7-10 years and 800 million dollars to bring a new drug to market. Accordingly, pharmaceutical companies are seeking a safer and economical ways to hasten drug development while minimizing the toxicity failure rate.

Drug compound toxicity can result in damages to DNA in the form of gene mutations, large scale chromosomal alterations, recombination and numerical chromosomal changes. Genotoxicity tests are in vitro and in vivo tests done in bacterial, mammalian cells and animals to detect compounds that induce such damages directly or indirectly by various mechanisms. The positive compounds could be human carcinogens and/or mutagens that induce cancer and/or heritable defects. A drug can be toxic at different levels, but drug-induced mutagenesis of DNA, such as germ line mutations, underlies many long term adverse effects.

Despite the guidelines set by government regulatory authorities, there are cases of drug toxicity, including the recent issues concerning the COX-2 group of pain killers. The toxicity failure rate in the developmental pipeline has remained unimproved over the years contributing to the ever increasing costs of the process. During compound screening, preclinical testing involves both in vitro and animal assays that assess efficacy and potential side effects to predict how the agent will affect humans, but the cost and speed associated with these genotoxicity tests have prohibited the wider use and earlier testing to improve the screening efficiency. For example, a standard first step for detecting mutagenicity is the Ames test, developed almost more than 30 years ago. But even the improved version of the Ames test takes requires 2-4 days to process and costs $4,000 to $5,000 per test to complete. For this reason, Ames tests are often used in later stages of drug development.

Among the required genotoxicity test battery, a large component is evaluation of chromosomal damage, in vitro or in vivo, involving the tk locus using mouse lymphoma L5178Y cells or human lymphoblastoid TK6 cells, the hprt locus using CHO cells, V79 cells, or L5178Y cells, or the gpt locus using AS52 cells. The toxicology field uses the mutation events induced by compounds at these specific loci as representatives of the entire genome, hoping the genetic alterations induced at these loci would be an accurate assessment of the overall DNA damage of the genome, for the simplicity of the model system or just sheer lacking of other efficient and economic ways of evaluation. In an ideal situation, every time a compound's exposure time, dosage, testing cell sampling time or any testing parameter changes, the entire genome, not just a few representative gene loci, of the testing cells or system could be evaluated in detail for damage information with great efficiency and low cost in a standardized format. At least, it would be very beneficial a panel of multi-gene loci, such as one each from every single chromosome or key interested regions, could be analyzed without prohibitive cost and complexity increase. New technology platform that would allow such comprehensive pan-genomic toxicity assessment with efficiency would be greatly desirable.

In the area of DNA damage assessment, decades-old conventional cytogenetic analysis (from karytotyping, G-banding to various forms of FISH) techniques often rely on a spread of metaphase DNA, their resolution is limited to the megabase scale. Interface or fiber-FISH methods attempt to improve the resolution by using relaxed or partially stretched DNA but they are still hard to implement and present challenges when trying to extract quantitative spatial information. Powerful as these techniques are, they suffer from poor control of the processes since they lack consistency and repeatability, hence are ultimately subject to the skill of the technician making them difficult to scale up for faster and cheaper genotoxicity tests.

Other recent attempts trying to improve the linearization of individual DNA molecules using surface "combing", optical tweezer, fluidic hydrodynamic focusing flow chip formats have reflected the desire to further improve the assay consistency, standardization and cost feasibility. Unfortunately, the methods of the target DNA elongation are not inherently well controlled, the molecule elongation state is often transient, non-uniform and inconsistent, deeming complicated analytical process. Such variability limits the application of this group of single molecule analysis approach for large scale screening of chromosomal DNA structural damages in genotoxicity tests.

Electrophoresis is also employed to separate polymers of various molecular weights based on their varying mobility using gels such as agarose or polyacrylamide. In the case of large polymer fragments, the separation time could take hours or even days. Single cell electrophoresis assays are routinely used to assess the damage of chromosomal DNA induced by toxic agents such as environmental toxins, radiation or agents used in chemotherapy. In a typical assay, termed the comet assay, often used in current genotoxicity tests, the cell is lysed within a gel matrix and then the DNA is electrophoresed and stained with a fluorescent dye. During electrophoresis, DNA fragments migrate away from the cell producing the shape of a comet tail. The geometry of the comet tail is related to the number of double stranded and single stranded breaks within the chromosomal DNA and thus provides a semi-quantitative measure of exposure to toxic agents experienced by the cell. Though this technique offers an assessment of the degree of damage, it is difficult to standardize and the data is subject to interpretation. Also, the fragments of chromosomal DNA remained entangled and cannot be distinguished from each other thus obscuring valuable information regarding the location of breaks or the size of individual fragments.

Other array based approaches such as Comparative Genomic Hybridization (CGH) have progressed in overcoming some aspects of resolution issues in detecting unbalanced genomic structural changes (amplification, deletion not translocation or inversion) however are limited to the issues inherit to comparative hybridization. New-generation sequencing technologies aim to achieve relatively fast sequence data on individual genetic molecules in massive parallel reads; however, molecules analyzed under such techniques must be fragmented into relatively short reads (~25 bps) with sequence data generated computationally, often by minimizing the tiling path of overlapping reads. A drawback of this approach is that gross genetic changes, usually at much larger scale, can often be obscured because each individual fragment is removed from the context of the entire genome. This is especially relevant in the case of complex genomes with regions of massive repetitive elements and gene copy number polymorphism. Accordingly, such techniques lack the ability to provide information regarding the whole of a genome, as opposed to a discrete region within the genome.

Molecular combing techniques have leveraged work in cytogenetics to generate more detailed analysis at the single molecule level. In molecular combing, DNA is elongated by means of a receding fluid meniscus as a droplet of solution is allowed to dry on a surface. The solute will migrate towards the boundaries of the droplet in a phenomenon known as the 'coffee-stain' effect (Deegan 1997). In the case of DNA in a buffer solution, the DNA is tethered to the surface randomly at the boundaries of a liquid phase and then elongated by the shear force of the receding meniscus. Unfortunately, this method of stretching is not inherently well controlled, and DNA samples on different microslides can never be "combed" identically, and there is no way to predict the degree, uniformity of stretching or placement of the molecules on a surface. DNA molecules often overlap each other with imperfect linearization (as they are not physically separated), and their ends often recoil upon themselves once they are released from the meniscus, leaving incompletely-stretched DNA molecules. Such variability accordingly limits the application of the combing approach to large scale screening of patients.

Other attempts to standardize the linearization of individual DNA molecules using fluidic biochip platforms proved relatively inefficient in effecting the desired linearization. DNA would often fold back on itself or even retain its free solution Gaussian coil conformation (essentially, a ball of yarn). The resolution of such techniques, furthermore, is poor, because the elongation of the DNA is often transient, non-uniform and inconsistent, and images used in analysis must be captured while the DNA moves at a high enough velocity to sustain its elongated state. In addition, because these designs are based around a single channel through which flow molecules past an optical detector, their throughput is severely limited.

Accordingly, there is a need for efficient determination of the sizes and composition of fragments of DNA or other macromolecules by linearizing and analyzing such molecules. Such methods would have immediate use in diagnostic and in treatment applications.

It would be desirable to use a minimal amount of sample, perhaps as little as a single cello This would greatly advance the ability to monitor the cellular state and understand the genesis and progress of diseases such as the malignant stage of a cancer cell or the degree of toxicity of a stimulus leading to apoptosis. There is also a related need for devices capable of performing such methods.

SUMMARY OF THE INVENTION

In meeting the challenges for analyzing the size and composition of DNA segments, the instant invention provides methods for confining, linearizing and then analyzing such molecules as well as devices capable of performing such methods.

First provided are nanofluidic devices capable of manipulating a single elongated macromolecule, comprising: a substrate comprising a surface and one or more fluidic nanochannel segments disposed substantially parallel to the surface, wherein at least one of the fluidic nanochannel segments is capable of containing and elongating at least a portion of a macromolecule residing within at least a portion of the fluidic nanochannel segment, and wherein each of the fluidic nanochannel segments has a characteristic cross-sectional dimension of less than about 1000 nm and a length of at least about 10 nm; and at least one viewing window, wherein the viewing window is capable of permitting optical inspection of at least a portion of the contents of the one or more fluidic nanochannel segments.

Also provided are methods for characterizing one or more macromolecules using a nanofluidic device, comprising translocating at least a portion of at least one region of the macromolecule through a fluidic nanochannel segment disposed substantially parallel to a surface of a substrate, wherein the fluidic nanochannel segment is capable of containing and elongating at least a portion of a region of the macromolecule, and wherein the fluidic nanochannel segment has a characteristic cross-sectional dimension of less than about 1000 nm and a length of at least about 10 nm; and monitoring, through a viewing window capable of permitting optical inspection of at least a portion of the contents of the fluidic nanochannel segment, one or more signals related to the translocation of one or more regions of the macromolecule through the nanochannel; and correlating the monitored signals to one or more characteristics of the macromolecule.

Further provided are devices, comprising A device, comprising: a substrate comprising a surface and one or more fluidic nanochannel segments disposed substantially parallel to the surface, wherein at least one of the fluidic nanochannel segments is capable of containing and elongating at least a portion of a macromolecule residing within at least a portion of the fluidic nanochannel segment, and wherein each of the fluidic nanochannel segments has a characteristic cross-sectional dimension of less than about 1000 nm and a length of at least about 10 nm; and wherein at least a portion of at least one fluidic nanochannel segment is illuminated by one or more excitation sources.

Additionally disclosed are macromolecular analysis devices, comprising one or more nanochannels disposed on a surface, one or more of the nanochannels having a width of less than about 1000 nm, and one or more of the nanochannels being defined by one or more borders and being capable of constraining at least a portion of the macromolecule so as to maintain in linear form that portion of the macromolecule.

Also provided are methods of analyzing macromolecules, comprising disposing one or more macromolecules onto a surface having one or more nanochannels capable of constraining at least a portion of the macromolecule so as to maintain in linear form that portion of the macromolecule; subjecting the one or more macromolecules to a motivating force so as to elongate at least a portion of one or more macromolecules within one or more nanochannels; and monitoring one or more signals evolved from one or more of the macromolecules.

The present invention also teaches methods of of fabricating a macromolecular analysis device, comprising defining one or more nanochannels on a surface by disposition of two or more borders, one or more of the borders being capable of constraining a macromolecule, and one or more of the nanochannels having a width of less than about 1000 nm.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

FIG. 3A depicts the fluorescent signals of the molecules as they flow along the channels, and using a data analysis algorithm, the number of macromolecules and their lengths can be determined;

FIG. 3B illustrates a plot of fluorescent signal intensity versus time of the macromolecules in FIG. 3A as they pass by the slit, FIG. 3D illustrates a plot of fluorescent signal intensity versus time of the macromolecules in FIG. 3C as they pass by the slit—in both cases, information regarding the distribution of macromolecule size can be determined from the detected signal;

FIG. 6A illustrates an example of a macromolecule flowing into and being at least partially elongated by a nanochannel device in which the nanochannels are covered by a cap—following elongation, the macromolecule is adhered to the surface and the cap is removed, see FIG. 6B, exposing the elongated region of the macromolecule and making the elongated region of the macromolecule available for additional analysis, processing, treatment, and the like;

(FIG. 9B) a nanotrack or nanolane where the boundaries of the track are defined by variations in the surface properties;

DETAILED DESCRIPTION OF ILLUSTRATIVE EMBODIMENTS

Figure 1A:
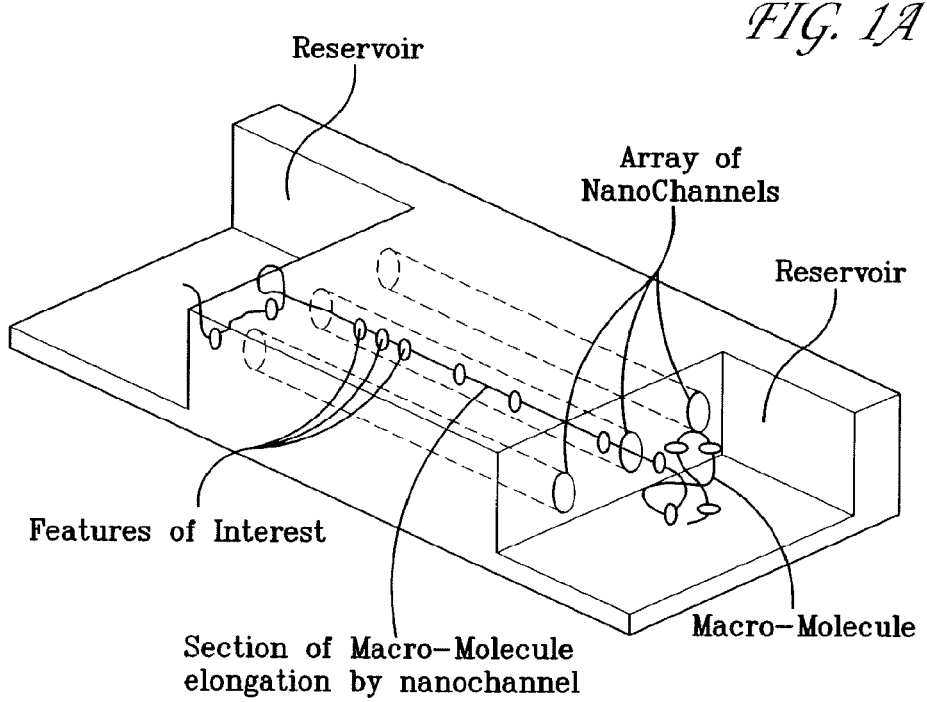
FIG. 1A illustrates detection of a macro-molecule flowing through a nanochannel device where passage of the macromolecule through the nanochannel is recorded by exciting features of interest to fluoresce with an excitation source, and then sensing the fluorescence with a photon detection device and this fluorescent signal is then correlated along the length of the macromolecule.

The present invention may be understood more readily by reference to the following detailed description taken in connection with the accompanying figures and examples, which form apart of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

TERMS

As used herein, the term "channel" means a region defined by borders. Such borders may be physical, electrical, chemical, magnetic, and the like. The term "nanochannel" is used to clarify that certain channels are considered nanoscale in certain dimensions.

As used herein, the term "biomolecule" means DNA, RNA, protein, and other molecules of biological origin.

Nanochannels having diameters below 200 nm have been shown to linearize double-stranded DNA molecules, thus preventing the molecule from bending back on itself and completely precluding the native Gaussian coil configuration normally assumed in free solution. (Cao et al., APL, 2002a) Such conformational constraints are ideal vehicles for single molecule DNA analysis. (Cao et al., APL, 2002b). Nanochannels have been shown to routinely linearize fragments that are ranged in size from several hundred kilobases to megabases (Tegenfeldt et al., PNAS, 2004). Furthermore, the nature of fluidic flow in a nanoscale environment precludes turbulence and many of the shear forces that would otherwise fragment long DNA molecules. This is especially valuable for macromolecule linear analysis, especially in molecular analysis of genomic structural pattern changes with specific probes or non-specific barcoding labeling schemes and features of interests such as epigenomic biomarkers of CpG islands clusters.

These favorable characteristics further open the possibility of long range linear sequencing applications in which intact native DNA is used without fragmentation or subcloning. In addition, there is no limit of the read length or capacity as the parallel or interwoven nanochannels could be fabricated as long as 30 cm long, with a density greater than tens of thousands of channels per cm. Most importantly, entrapping and linearizing polymers like genomic DNA in nanochannels that are enclosed or non-enclosed, made by a well controlled fabrication or self-assembly approach, would allow ultimately allow the highly desired standardization of quantitative measurements of polymers at the single molecule level.

Nanochannels are distinct from nanopores in that nanopores have a very low aspect ratio (length/diameter) while nanochannels have a high aspect ratio. Typically, nanopores are 0.5 to 100 nm in diameter but only a few nm in length. Nanochannels may be of similar diameter but are at least 10 nm in length.

A nanochannel's effective diameter is dictated by the radius of gyration and persistence length of the polymer to be analyzed so as to ensure complete or near complete linearization of the portion of the polymer inside the nanochannel. Semi-flexible polymer chains bundle up into a random coil in free solution with a radius of gyration defined as $Rg=(Lp/6)^{1/2}$ wherein L is the calculated contour length and p is the persistence length of the polymer chain. A λ-DNA segment 16.5 microns in length—and containing approximately 500 persistence lengths—has a radius of gyration of approximately 734 nm. Chen, et al., Probing Single DNA Molecule Transport Using Fabricated Nanopores, *Nano Letters*, 2004, 4, 11, 2293-2298. A 4681 base-pair double-stranded DNA fragment has a radius of gyration of approximately 280 nm. Dietrich, et al., Advances in the Development of a Novel Method to be used in Proteomics using Gold Nanobeads, *Ultrasensitive and Single-Molecule Detection Technologies*, edited by Jorg Enderlein, et al, Proc. of SPIE Vol. 6092, 6092C (2006). Thus, a nanochannel may have a diameter smaller than twice the radius of gyration of the analyzed polymer coil. Nanochannels of such dimension begin to exert entropic confinement on the free fluctuating polymer coil, causing it to elongate and/or linearize.

Biological molecules such as DNA or RNA fragments are long polymers and their size often carries significant information that is unknown in a heterogeneous biological sample. Electrophoresis is usually employed to separate polymers of various molecular weights based on their varying mobility using gels such as agarose or polyacrylamide. In the case of large polymer fragments, the separation time could take hours or even days. For the purposes of this application biomolecules such as DNA, RNA, protein, or other single molecules are referred to as macromolecules.

Long nanochannels with sufficiently small dimensions as described above are effective for elongating these polymer chains in a linear form through entropic confinement, rendering their apparent contour length quantitatively correlated to their individual molecular weight.

This is especially important for applications such as genotoxicity—a determination of the genetic damage inflicted by a particular compound or compounds—in which the size and sequence of one or more critical chromosomal DNA fragments carries important information regarding the stage of apoptosis and level of exposure to toxic stimuli. Genotoxicity testing is of particular importance in pharmaceuticals, see Guidance For Industry S2B Genotoxicity: A Standard Battery for Genotoxicity Testing of Pharmaceuticals, International Conference on Harmonization of Technical Requirements for Registration of Pharmaceuticals for Human Use, 1997. It is recommended, see id., that genotoxicity testing in pharmaceuticals involve (1) a test for gene mutation in bacteria; (2) an in vitro test with cytogenic evaluation of chromosomal damage with mammalian cells or an in vitro mouse lymphoma tk assay; and (3) an in vivo test for chromosomal damage using rodent hematopoetic cells. Accordingly, a method for efficiently performing genotoxicity testing would have immediate applicability to the pharmaceutical industry.

Determining the size of DNA fragment could provide further information as to where factors, caused directly or indirectly by the said stimuli, are interacting with the long polymers; or where the damage would occur at specific locations in correlation to specific conditions. It has been reported that during apoptosis, chromosomal DNA is first digested into fragments that are 50-300 kbps in size. A subsequent digestion step results in fragments that are <1 kbp (Nagata et al., *Cell Death and Diff.* 2003).

In the area of toxicogenomics, single cell electrophoresis assays are routinely used to assess the damage of chromosomal DNA induced by toxic agents such as environmental toxins, radiation or agents used in chemotherapy. In a typical assay termed the comet assay, the cell is lysed within a gel matrix and then the DNA is electrophoresed and stained with a fluorescent dye.

During electrophoresis, DNA fragments migrate away from the cell producing the shape of a so-called comet tail. The geometry of the comet tail is related to the number of double stranded and single stranded breaks within the chromosomal DNA and thus provides a semi-quantitative measure of exposure to toxic agents experienced by the cello Though this technique offers single cell analysis by definition, it is difficult to standardize and the data is subject to interpretation. Also, the fragments of chromosomal DNA remain entangled and cannot be distinguished from each other, thus obscuring information regarding the location of breaks or the size of individual fragments.

Lastly, DNA damage assessment caused by radiation is another important field. Besides cases of accidental exposure to various forms of radiation, more than half of all cancer patients receive radiation therapy at some point. Determining the correct radiation dose to minimize side effects while retaining maximum effectiveness in killing a tumor is challenging. A typical radiation treatment plan is 30 sessions; however, in current practice a treatment plan is basically set from the beginning, based on data from the so-called best treatment for the "average" patient and not what might be appropriate for each individual. Finding new diagnostics and therapeutics to optimize radiation therapy toward personalized medicine in the radiation oncology field is a high priority.

At the molecular level, radiation therapy kills tumor cells by essentially breaking up their DNA. Detecting this genetic damage in a manner that could give physicians valuable feedback can help adjust subsequent treatment. In current radiation dosimetry assays, genomic damage assessment and cell viability after exposure were often assayed in a relatively tedious and slow fashion without direct quantitative information of what is going on inside the tumor or surrounding healthy cells.

As applied to radiation therapy, a nanochannel array based device could physically unwind genomic DNA samples from their natural coiled structure to a linear form and analyze the population characteristics such as degree of fragmentation damage. This method can monitor changes in the integrity of the DNA samples taken from a tumor and surrounding tissue and quantify the damage in an instantaneous fashion to better guide treatment with "functional" tumor information.

In one aspect, the present invention provides nanofluidic devices capable of manipulating a single elongated macromolecule, comprising: a substrate comprising a surface and one or more fluidic nanochannel segments disposed substantially parallel to the surface, wherein at least one of the fluidic nanochannel segments is capable of containing and elongating at least a portion of a macromolecule residing within at least a portion of the fluidic nanochannel segment, and wherein each of the fluidic nanochannel segments has a characteristic cross-sectional dimension of less than about 1000 nm and a length of at least about 10 nm; and at least one viewing window, wherein the viewing window is capable of permitting optical inspection of at least a portion of the contents of the one or more fluidic nanochannel segments.

Figure 11:
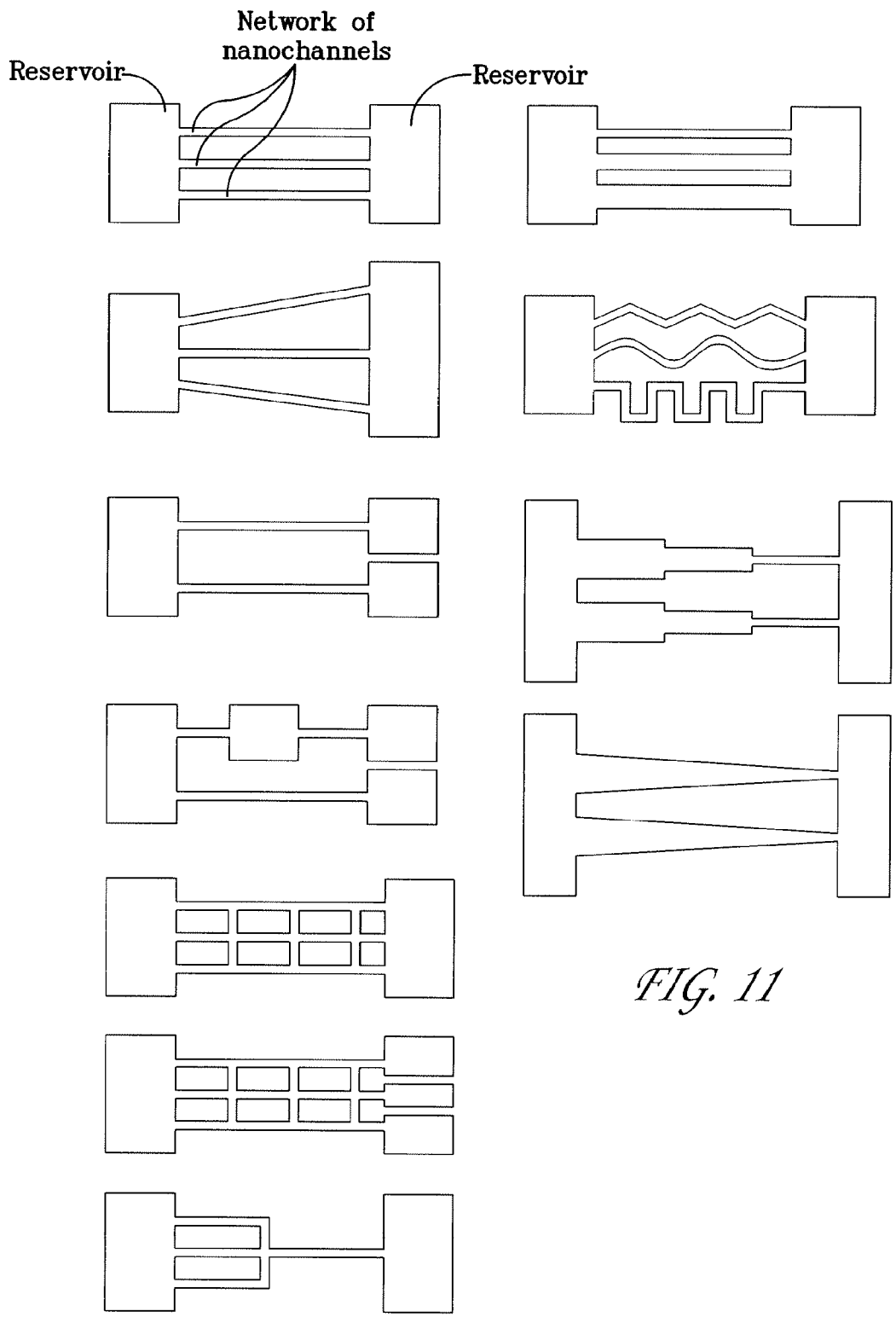
FIG. 11 illustrates various configurations of nanochannel networks, and depicts networks where nanochannels are in fluidic communication with each other and where the nanochannels are disposed parallel to one another.
Figure 12B:
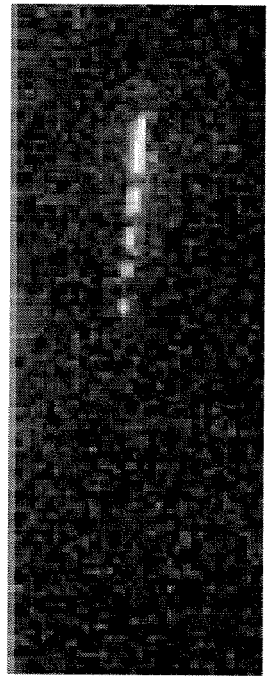
FIG. 12B is a closer view of the DNA fragments boxed-in in FIG. 12A.
Figure 12C:
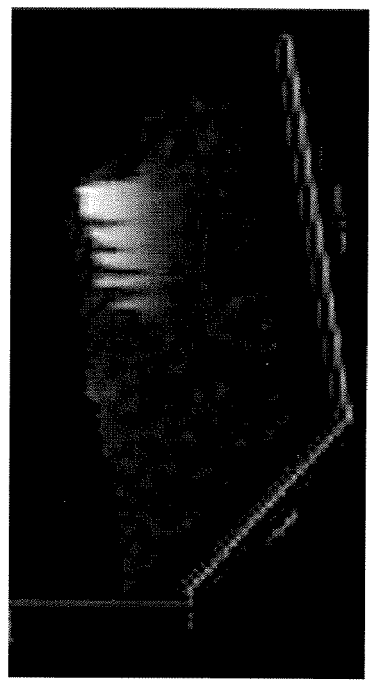
FIG. 12C depicts the image intensity as a function of position for the boxed-in DNA fragments of FIGS. 12A and 12B.
Figure 12A:
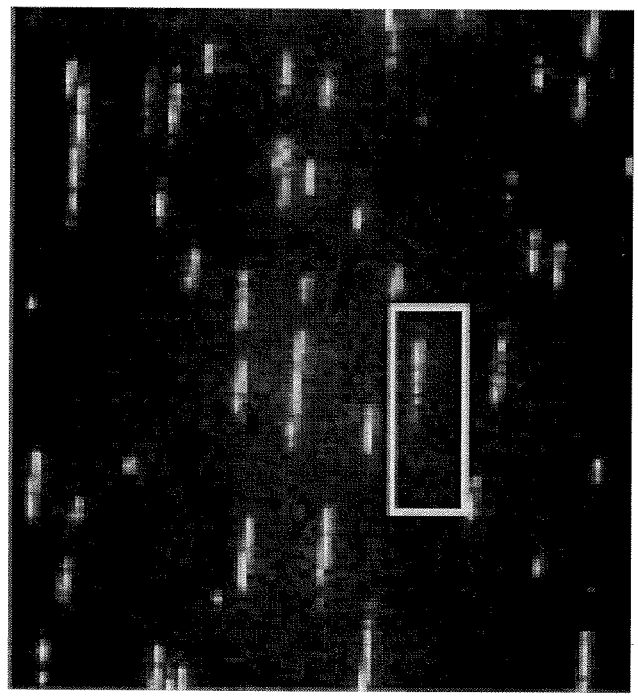
FIG. 12A illustrates DNA fragments of various sizes.
Figure 13B:
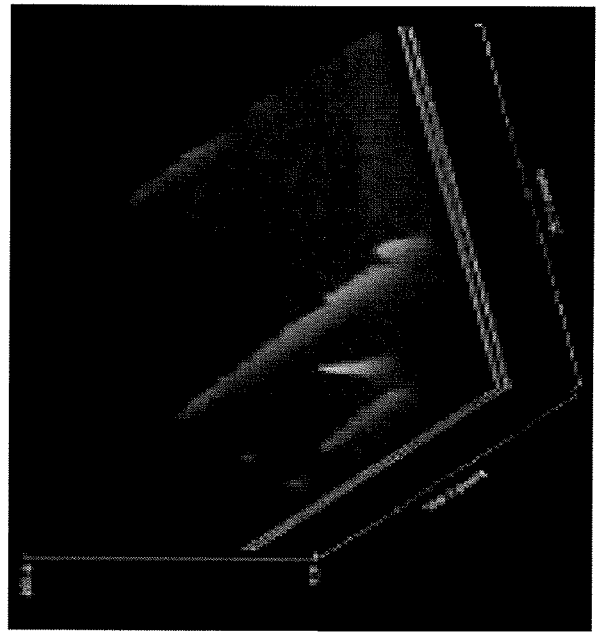
FIG. 13B depicts the image intensity as a function of position for the DNA fragments of FIG. 13A.
Figure 13A:
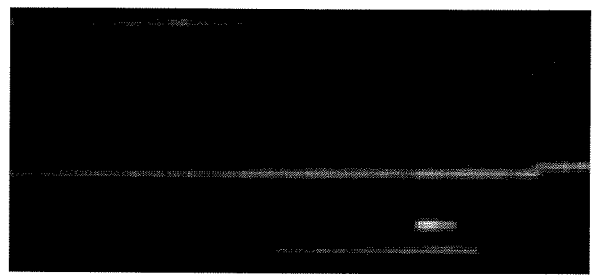
FIG. 13A depicts several labeled DNA fragments of varying lengths.
Figure 14:
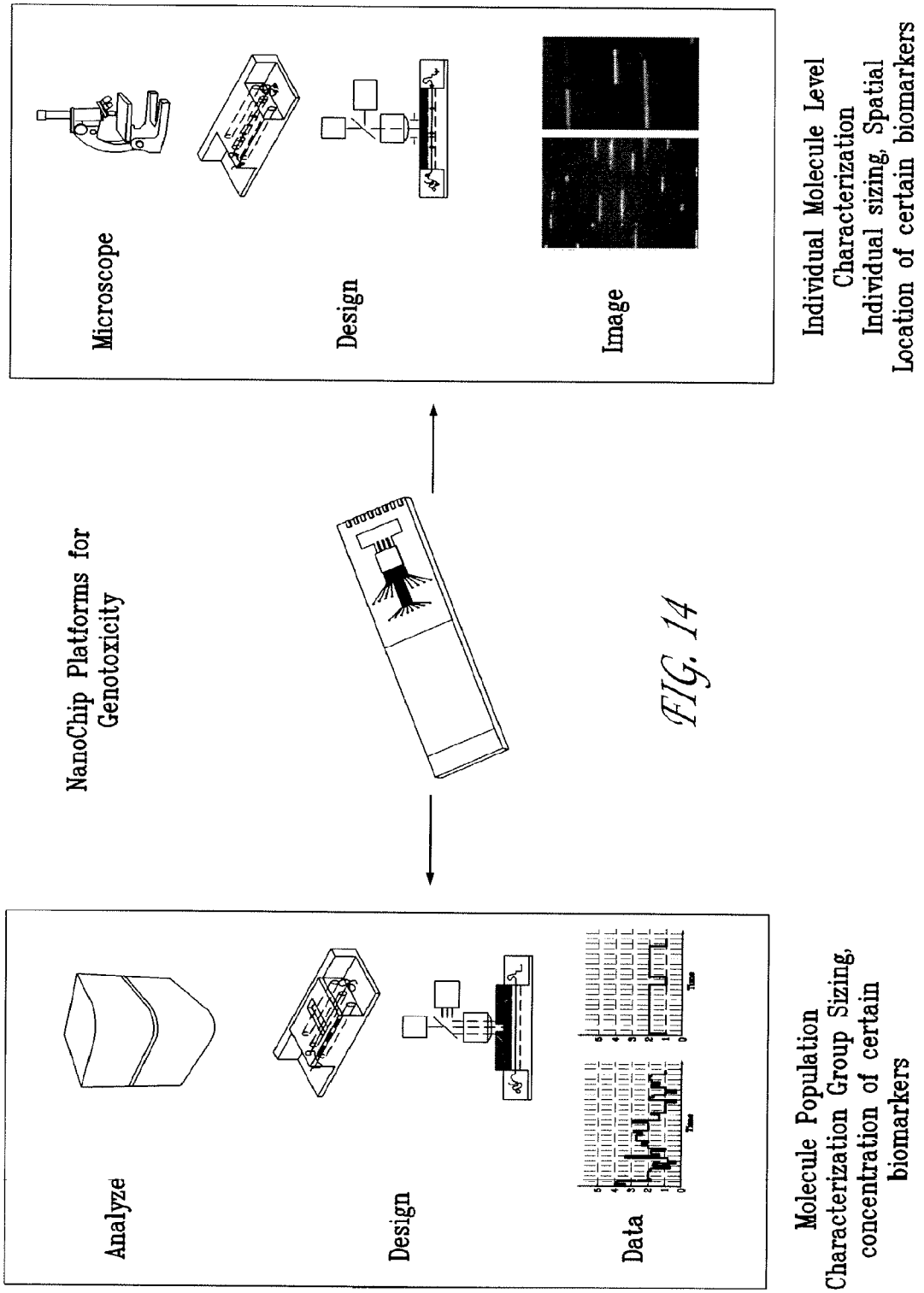
FIG. 14 depicts two applications for the disclosed nanochannel devices and methods—the left-hand panel of FIG. 14 depicts the use of the nanochannel device to characterize a population of macromolecules, which characterization can include the distribution of molecule sizes within the population or the concentration of certain biomarkers within the group, and the right-hand panel of FIG. 14 depicts the use of the nanochannel device to characterize an individual molecule, including the size of the individual molecule and the spatial location of biomarkers on the single molecule.
Figure 15:
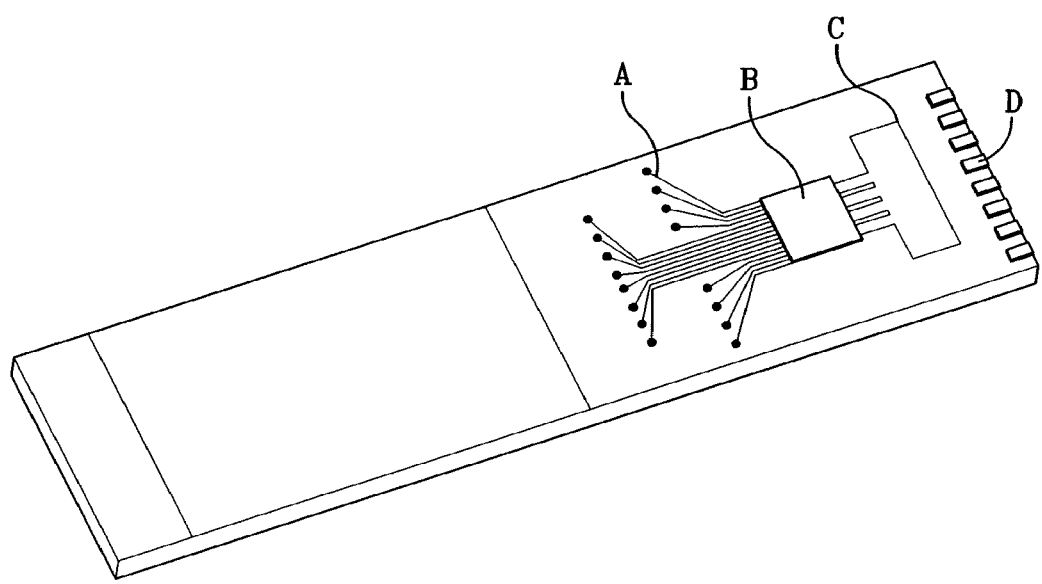
FIG. 15 is a schematic view of a representative nanochannel device, wherein (A) indicates sample inlets, (B) indicates the nanochannels disposed on the device (C) indicates a waste region for receiving sample that has flowed through the nanochannels, and (D) indicates structures capable of forming electrical or other connections with other devices, apparatuses, and the like external to the nanochannel device.
Figure 16:
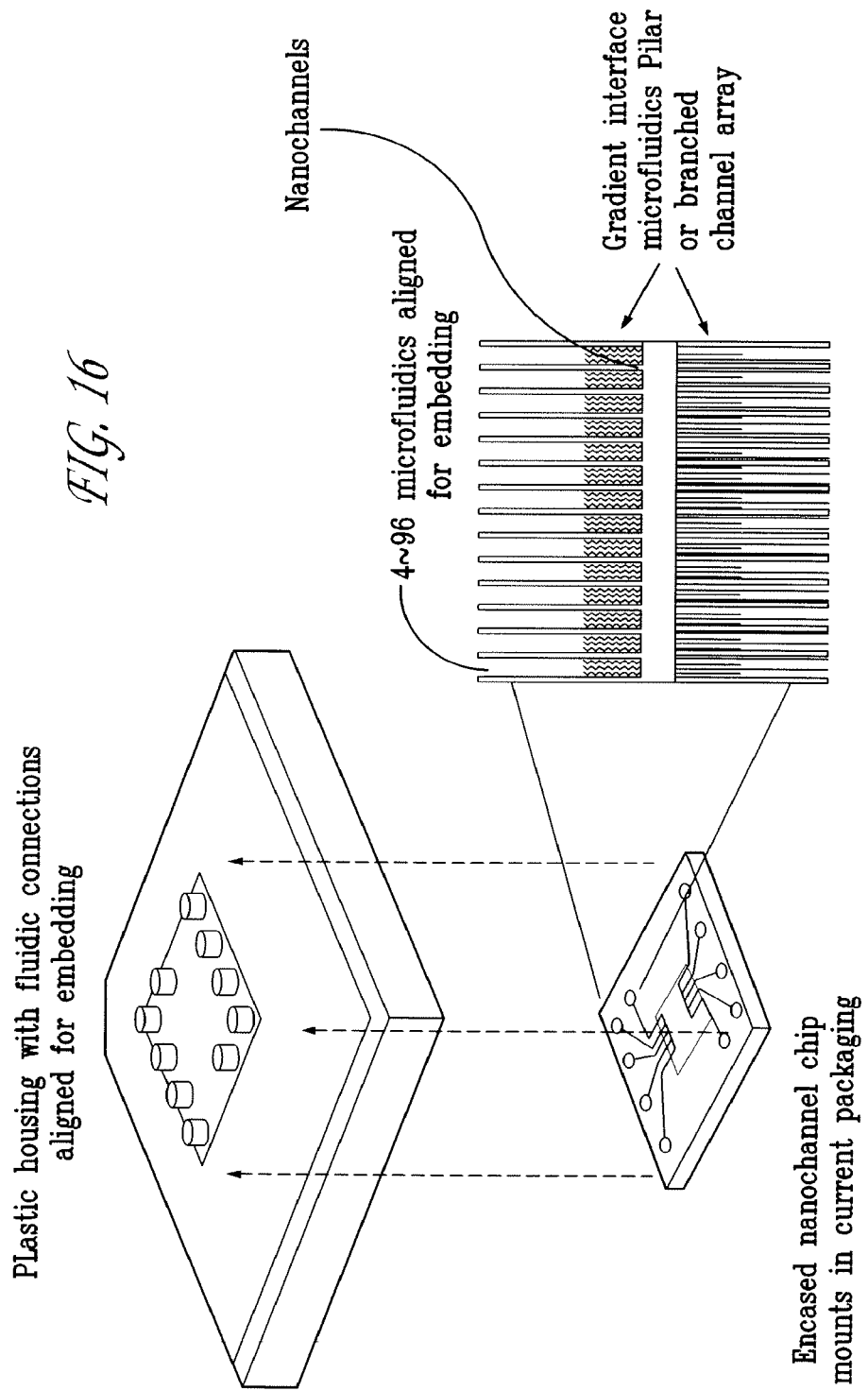
FIG. 16 is a schematic view of a nanochannel device mating to a plastic housing containing one or more connections aligned so as to interface the nanochannel device with other devices external to the device—FIG. 16 also provides a schematic view of an array of nanochannels, wherein the nanochannels interface with microfluidics as well as a set of pillars, where the pillars are capable of at least partially straightening one or more macromolecules before the macromolecules enter the nanochannels.

In some embodiments, as shown in FIG. 11, the fluidic nanochannel segments that are not fluidically connected to each other, and can in some cases be disposed essentially parallel on one another.

In other embodiments, also as shown in FIG. 11, at least a portion of the fluidic nanochannel segments are fluidically connected to each other. In some of these embodiments, the fluidic nanochannel segments fluidically connected to each other are disposed in a branching pattern or in a grid pattern. Certain patterns of nanochannels can be achieved by self-assembly techniques known to those in the art.

One or more of the fluidic nanochannel segments can, in some cases be curved in form, tortuous in form, or even have a varying cross-sectional dimension. It is contemplated that not all nanochannels are equivalent in cross-sectional dimension; in some case, at least one of the fluidic nanochannel segments comprises a cross-sectional dimension that is different than the cross-sectional dimension of another of the fluidic nanochannel segments.

It is also contemplated, see FIG. 11, that nanochannel segments can be interconnected or even vary in cross-section.

Substrates suitable for the present invention include metals, ceramics, polymers, glasses, silicons, semiconductors, plastics, dielectrics, SiGe, GaAs, ITO, fused silica, and the like. The optimal substrate will be dictated by the needs of the user.

Suitable fluidic nanochannel segments have a characteristic cross-sectional dimension of less than about 500 nm, or of less than about 200 nm, or of less than about 100 nm, or even of less than about 50 nm, about 10 nm, about 5 nm, about 2 nm, or even less than about than about 0.5 nm.

A fluidic nanochannel segment suitably has a characteristic cross-sectional dimension of less than about twice the radius of gyration of the macromolecule. In some embodiments, the nanochannel has a characteristic cross-sectional dimension of at least about the persistence length of the macromolecule.

Fluidic nanochannel segments suitable for the present invention have a length of at least about 100 nm, of at least about 500 nm, of at least about 1000 nm, of at least about 2 microns, of at least about 5 microns, of at least about 10 microns, of at least about 1 mm, or even of at least about 10 mm. Fluidic nanochannel segments are, in some embodiments, present at a density of at least 1 fluidic nanochannel segment per cubic centimeter.

Figure 10:
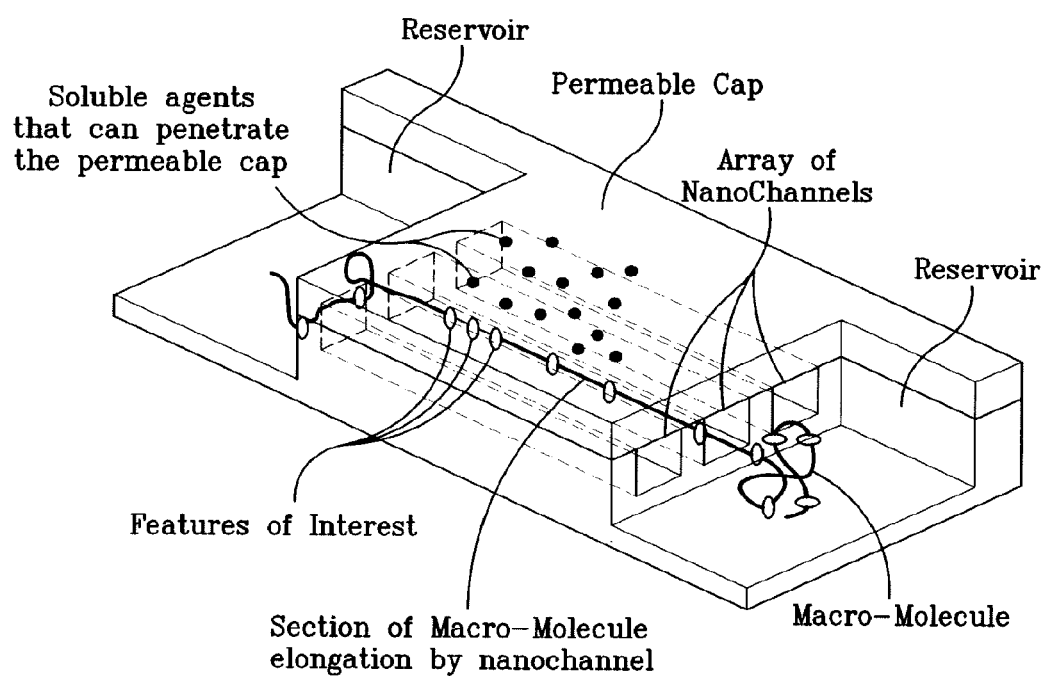
FIG. 10 illustrates macromolecules elongated in a nanochannel device in which the cap material is permeable to agents which can interact with the macromolecule while the macromolecule resides within a nanochannel—such a permeable cap can also be used to pre-treat nanochannels with agents in order that the agents interact with the macromolecules once the macromolecules enter into the pre-treated nanochannels.

Viewing windows of the invention can comprise a slit, a porthole, a square, or any combination thereof. In some configurations, the viewing window is removable, or permeable, see FIG. 10. Permeable windows are suitably capable of placing the contents of one or more fluidic nanochannel segments into fluid communication with the environment external to the fluidic nanochannel segment.

Figure 6A:
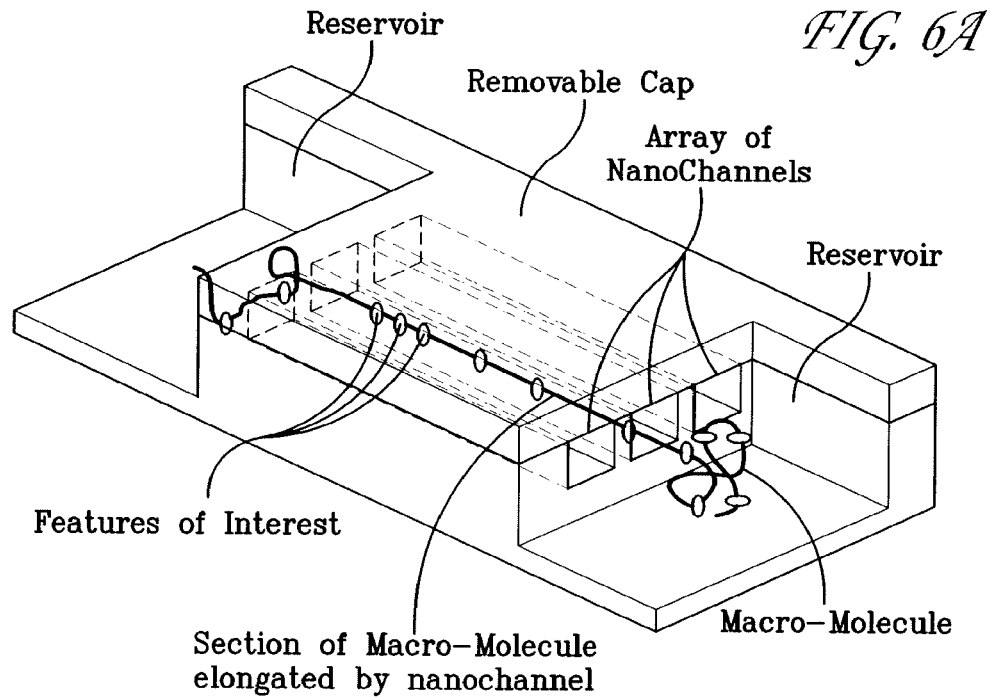
Figure 6B:
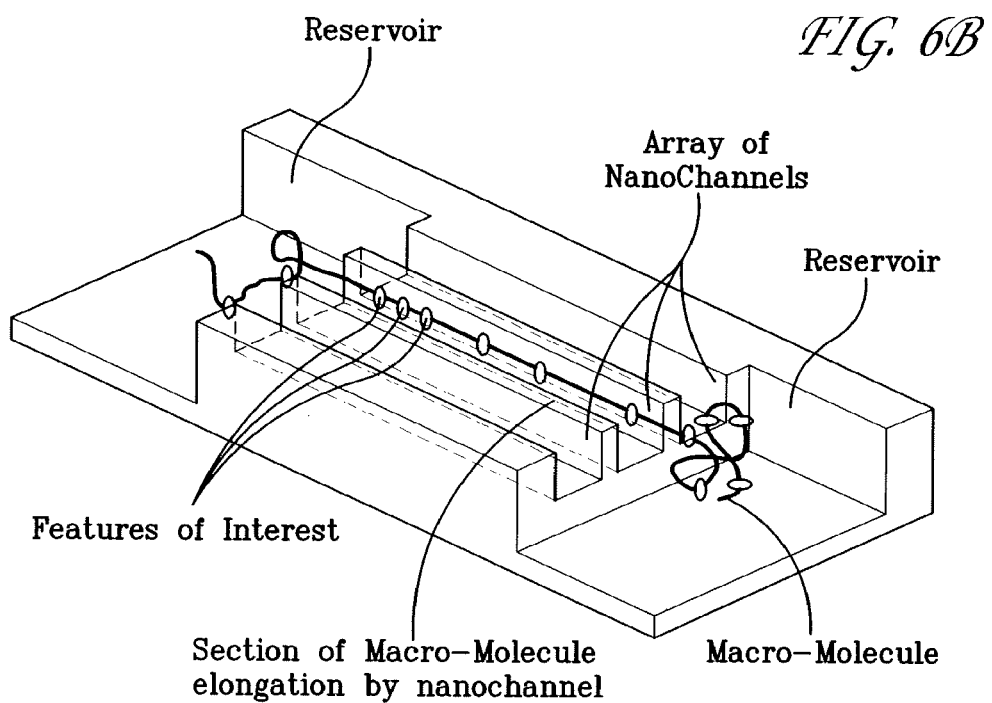
Figure 9A:
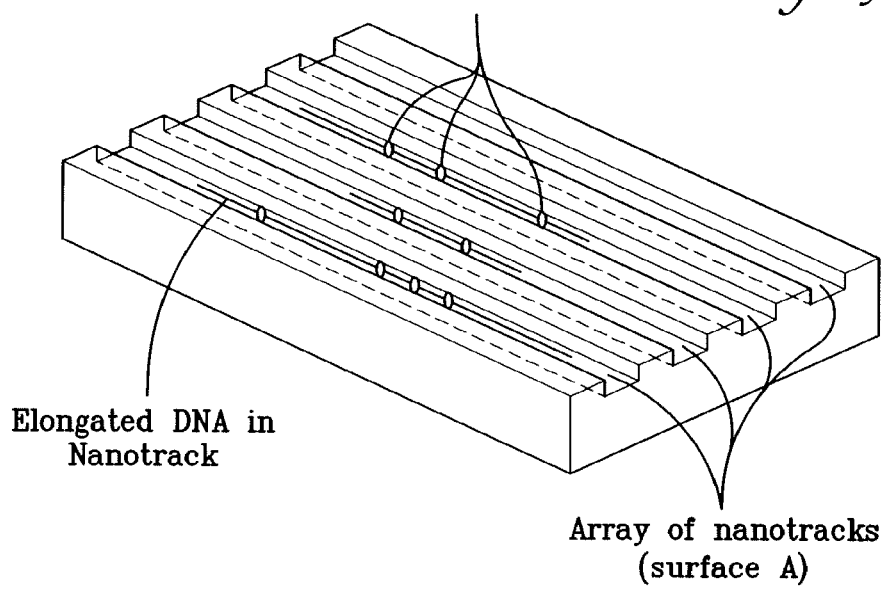
FIGS. 9A-B illustrate DNA molecules elongated in (FIG. 9A) a nanotrench where the boundaries of the trench are defined by a topological patterning of the surface.
Figure 9B:
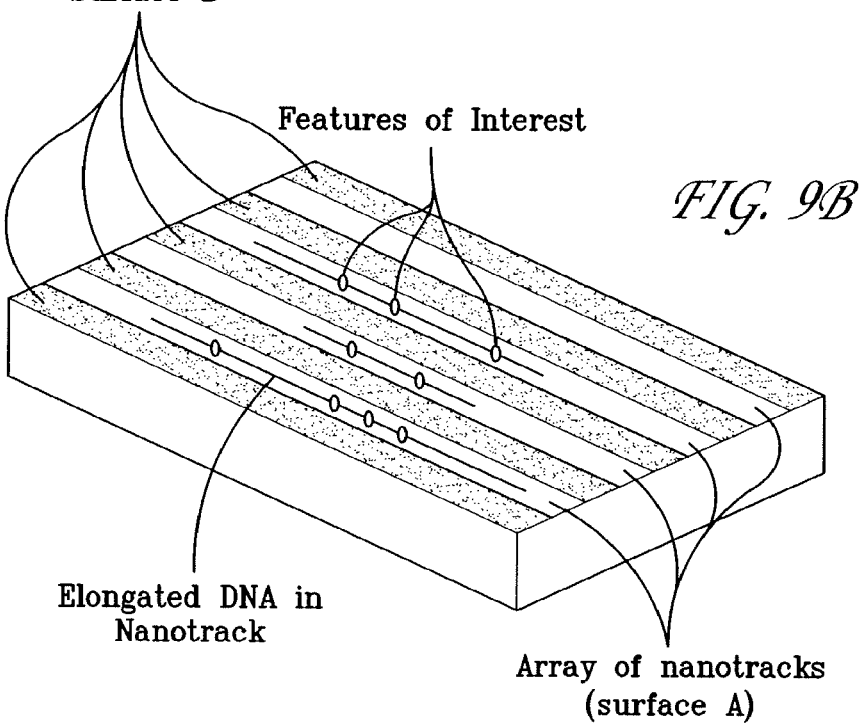

As shown in FIGS. 9A and 9B, fluidic nanochannel segments may be characterized as trenches, and some devises comprise a cap capable of covering at least a portion of at least one trench. See FIG. 6. In some embodiments, at least a portion of the cap is permeable to soluble analytes capable of interaction with a macromolecule residing in the fluidic nanochannel segment, FIG. 10, or is removable or even optically transparent. In some embodiments, one or more macromolecules are at least partially elongated in the fluidic nanochannel segment and remain in a substantially elongated form after the cap is removed. See FIG. 6B.

Figure 1B:
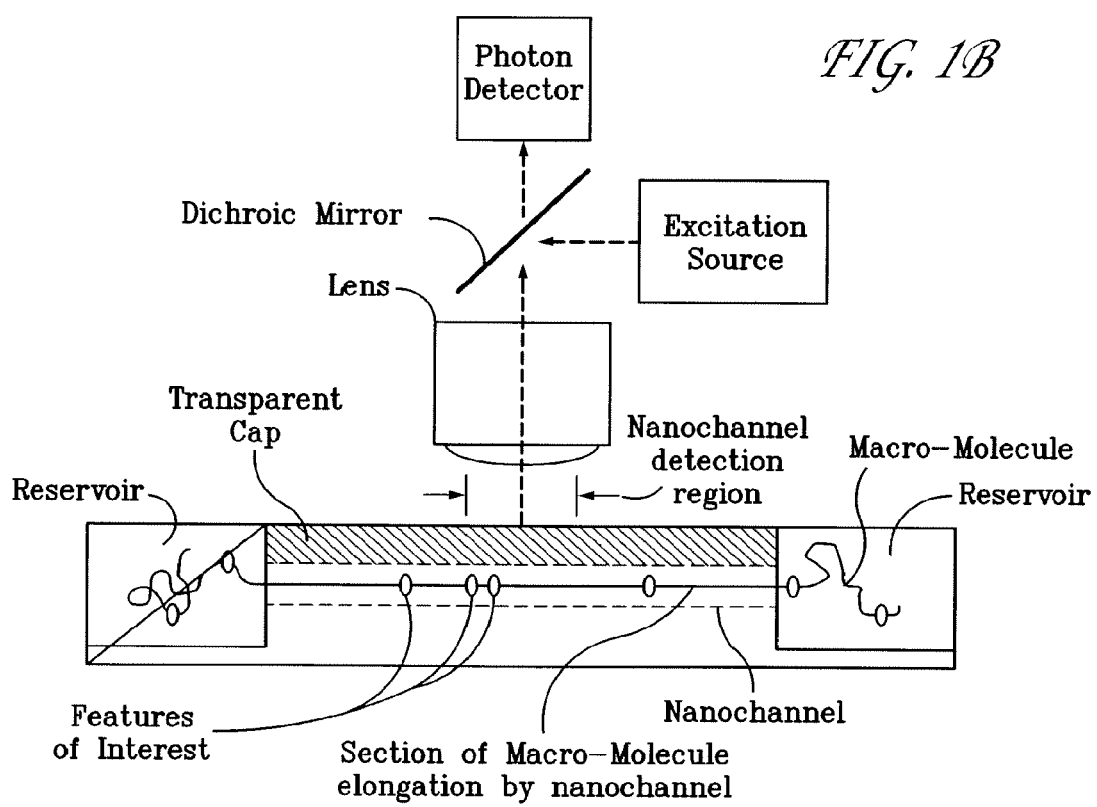
FIG. 1B illustrates a cross-sectional view of the device, where light from an excitation source illuminates the features of interest as they pass under the photon detector, which detector in turn monitors any photons emitted by the illuminated features.
Figure 2A:
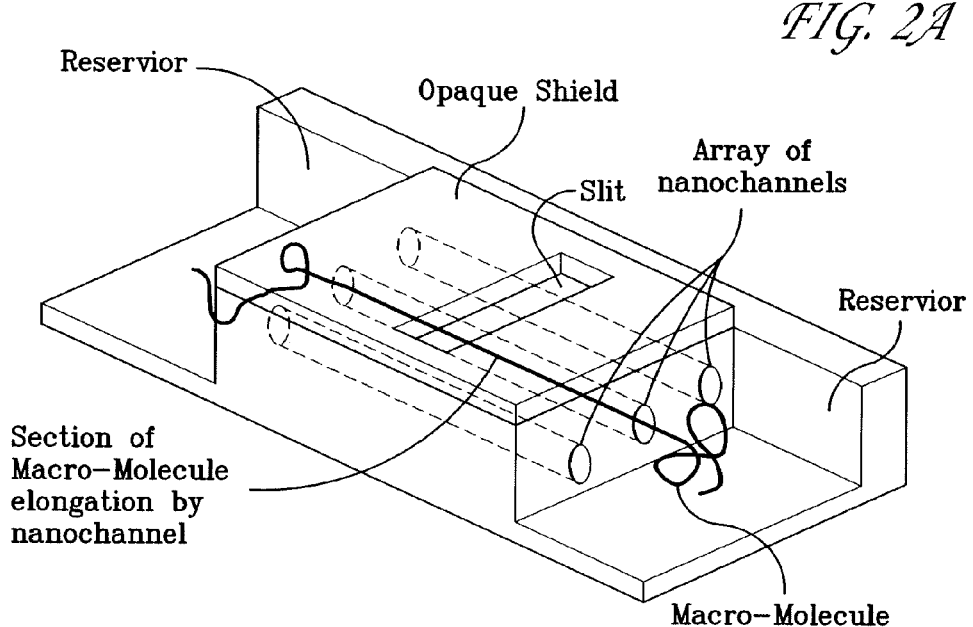
FIG. 2A illustrates detection of a macromolecule flowing through a nanochannel device, whereby the macromolecule is exposed to the excitation illumination passed through a slit, where the fluorescent signal is acquired from the region of the macromolecule in the nanochannel that is under the slit—by flowing the macromolecule through the nanochannel, a stream of fluorescent signals can be collected from the slit that can be used to determine characteristic features along the length of the macromolecule, as is shown in FIG. 2B.
Figure 2B:
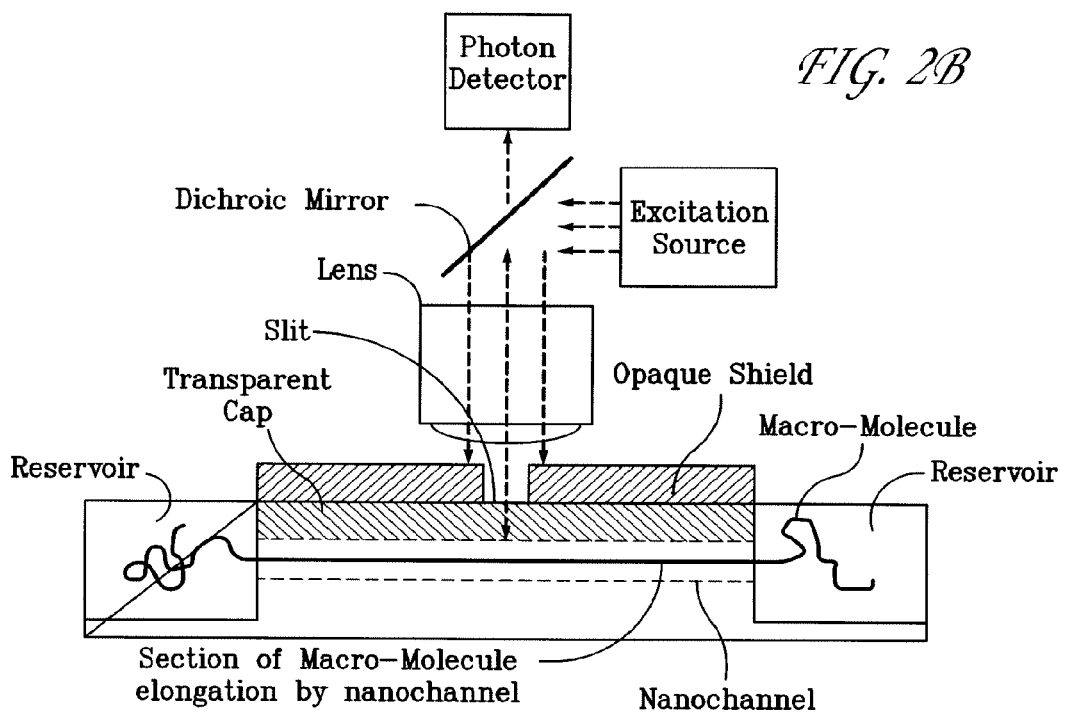
Figure 3A:
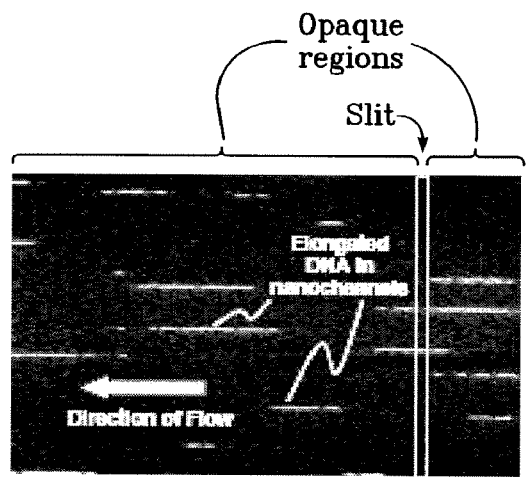
FIGS. 3A-D illustrate an example of how fluorescent signals from macromolecules flowing through nanochannels acquired using a slit can generate a stream of data.
Figure 3C:
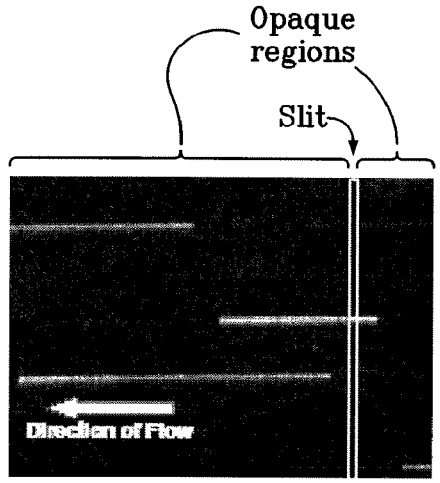
Figure 3B:
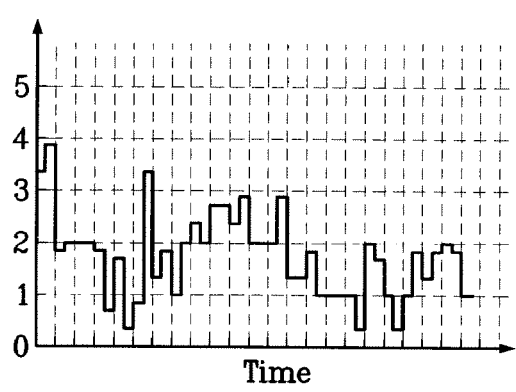
Figure 3D:
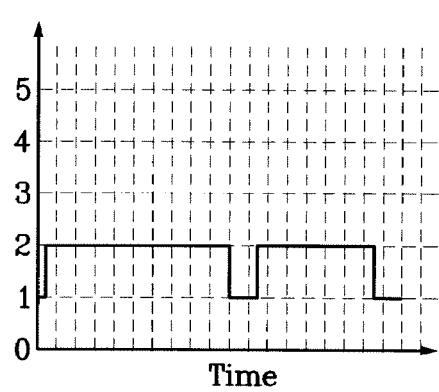
Figure 4A:
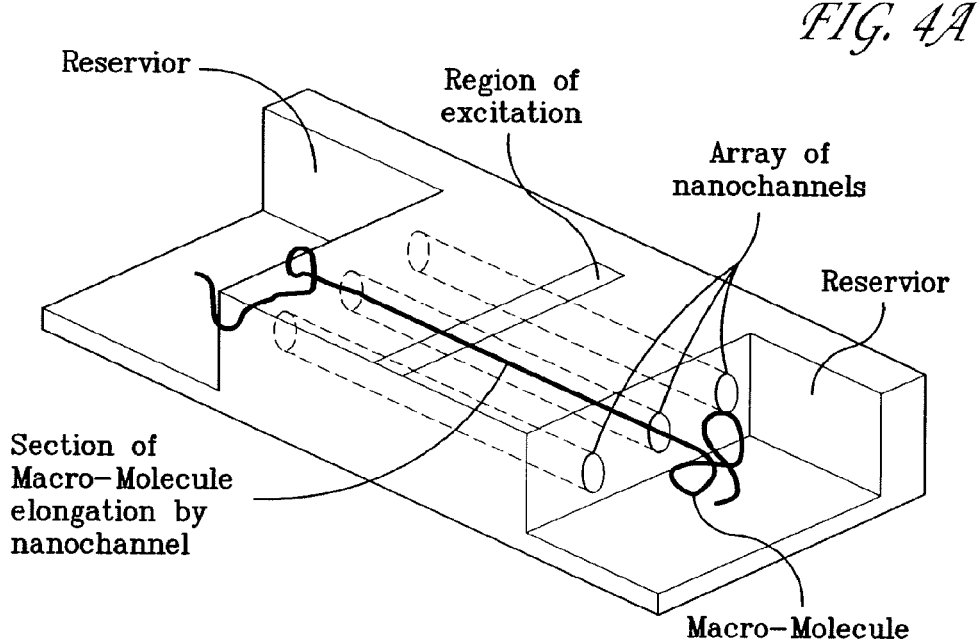
FIG. 4A illustrates an example of a macromolecule flowing through a nanochannel device, whereby the macromolecule is exposed to excitation illumination that is focused on a defined region of the nanochannels—in such an embodiment, the fluorescent signal is acquired from the region of the macromolecule in the nanochannel that is illuminated, and by flowing the macromolecule through the illuminated region, a stream of fluorescent signals can be collected from the macromolecule, FIG. 4B, that can be used to determine characteristic features along the length of the macromolecule.
Figure 4B:
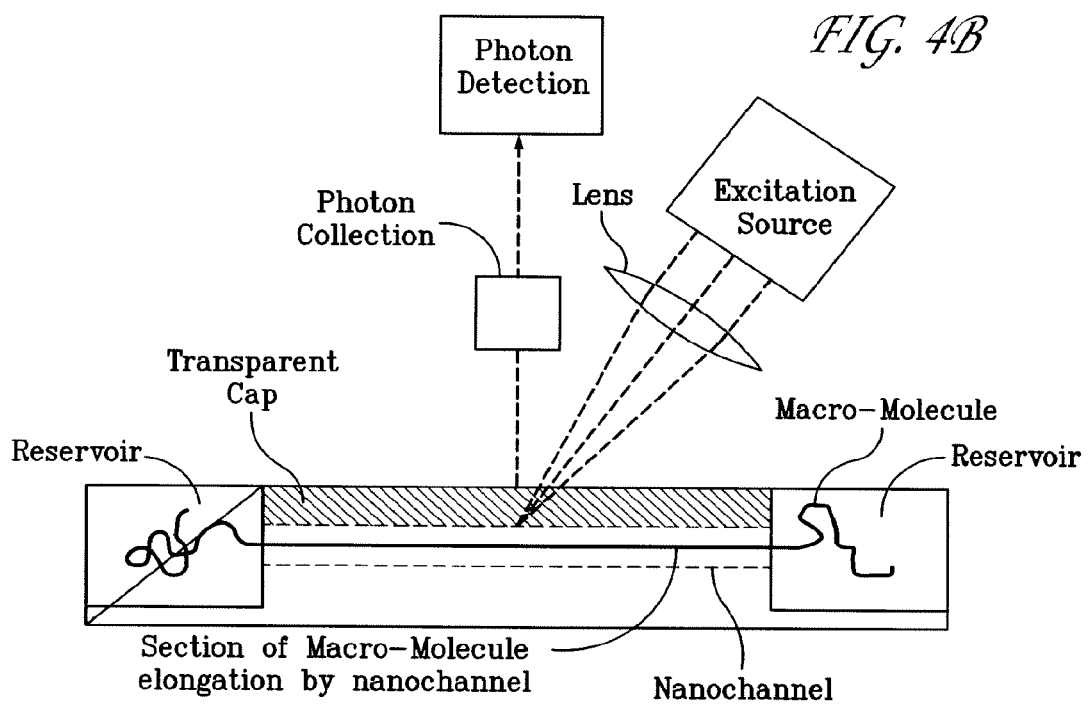
Figure 5A:
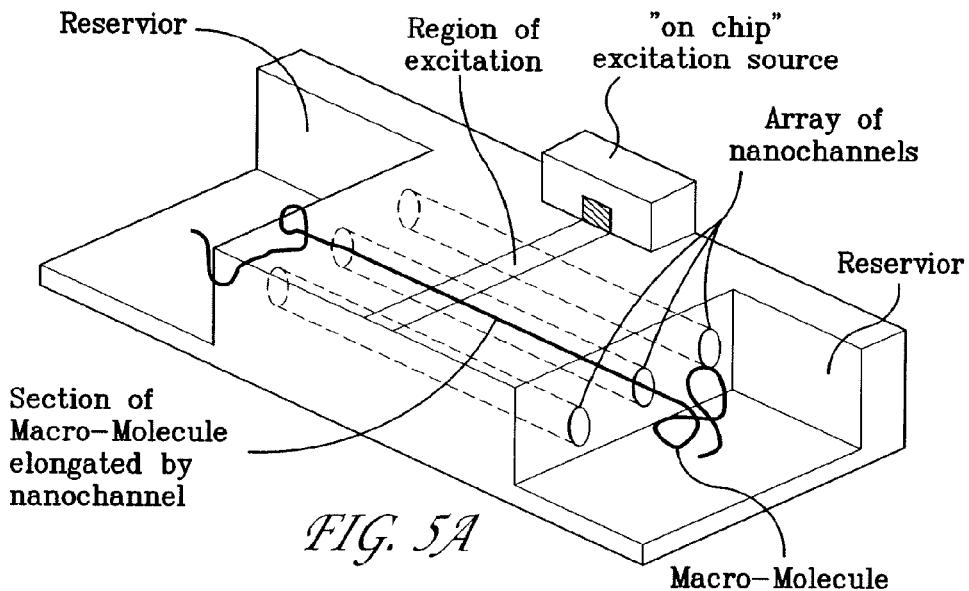
FIG. 5A illustrates a macromolecule flowing through a nanochannel device, whereby the macromolecule is exposed to an excitation illumination source that is integrated with the chip device—in this embodiment, the fluorescent signal is acquired from the region of the macromolecule in the nanochannel that is illuminated, and by flowing the macromolecule through the illuminated region, a stream of fluorescent signals is collected from the macromolecule, FIG. 5B, that can be used to determine characteristic features along the length of the macromolecule.
Figure 5B:
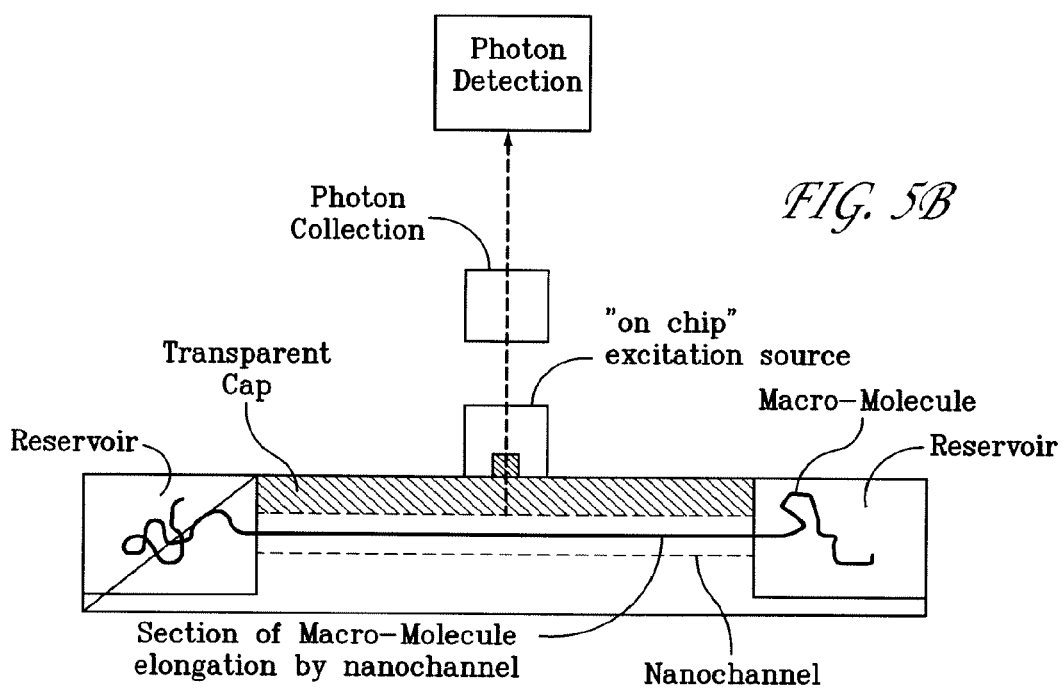

In other embodiments, FIG. 1, fluidic nanochannel segments are characterized as tunnels, and, in some cases can be characterized as a zone bordered by one or more regions having a surface chemistry. See FIG. 9B. Suitable surface chemistries includes a hydrophobic species, a hydrophilic species, a surfactant, a thiol, an amine, a hydroxyl, an alcohol, a carbonyl, a silane, and the like. Other surface chemistries are described elsewhere herein.

It is contemplated that one or more fluidic nanochannel segments is in fluid communication with one or more fluidic devises, such as conduits, pumps, filters, screens, occlusions, gels, heaters, splitters, reservoirs, and the like.

Macromolecules suitable for use in the device include polymers, double-stranded DNA, single-stranded DNA, RNA, polypeptides, biological molecules, proteins, and the like. Suitable polymers include homopolymers, copolymers, block copolymers, random copolymers, branched copolymers, dendrimers, or any combination thereof.

The present devices include, in certain embodiments, one or more connectors capable of placing the device in fluid communication with one or more apparatuses external to the device; suitable apparatuses include pump, conduits, filters, screens, gels, heaters, occlusions, splitters, reservoirs, or any combination thereof.

Also disclosed are methods for characterizing one or more macromolecules using a nanofluidic device, comprising: translocating at least a portion of at least one region of the macromolecule through a fluidic nanochannel segment disposed substantially parallel to a surface of a substrate, wherein the fluidic nanochannel segment is capable of containing and elongating at least a portion of a region of the macromolecule, and wherein the fluidic nanochannel segment has a characteristic cross-sectional dimension of less than about 1000 nm and a length of at least about 10 nm; and monitoring, through a viewing window capable of permitting optical inspection of at least a portion of the contents of the fluidic nanochannel segment, one or more signals related to the translocation of one or more regions of the macromolecule through the nanochannel; and correlating the monitored signals to one or more characteristics of the macromolecule.

The claimed methods can also include exposing at least one biological entity to an agent or agents of interest, to metabolites of such agents, to salts of the agents, and the like. Agents include dyes, labels, proteins, enzymes, probes, nucleotides, oligonucleotides, and similar species.

Exposure is accomplished by injecting, treating, spraying, transfecting, digesting, immersing, flowing, or applying the agent. As one example, a cell might could be incubated in a medium containing a dye agent for a period of time so as to expose the cell to that agent.

Biological entities suitably subjected to the claimed methods are not limited to cells; such entities may also include living creatures, biological molecules, proteins, and the like. Components of such entities may also be subjected to the claimed entities.

In some embodiments, the methods also include isolating one or more macromolecules from the biological entity. Isolating may be accomplished by means known to those of ordinary skill in the art. A non-limiting list of such means includes, for example, extracting, lysing, purifying, pulling, manipulating, reacting, distilling, electrophoresing, and the like.

Various macromolecules are suitably subjected to the claimed methods. Some of these macromolecules include proteins, single-stranded DNA, double-stranded DNA, RNA, siRNA, and the like. Polymers and other chain-structured molecules are also suitably used in the claimed methods.

Macromolecules used in the methods may also be divided the one or more macromolecules into two or more segments. In some cases, this enables more efficient processing or storage of the macromolecules.

Division of a macromolecule is accomplished by lasing, sonicating, chemically treating, physically manipulating, biologically treating, lysing, restricting, and the like. Those of ordinary skill in the art will be aware of methods suitable for dividing or otherwise segmenting or shortening a given macromolecule The methods further include binding a fluorescent label, a radioactive label, a magnetic label, or any combination thereof to one or more regions of the macromolecule. Binding may be accomplished where the label is specifically complementary to a macromolecule or to at least a portion of a macromolecule or other region of interest.

Translocating includes applying a fluid flow, a magnetic field, an electric field, a radioactive field, a mechanical force, an electroosmotic force, an electrophoretic force, an electrokinetic force, a temperature gradient, a pressure gradient, a surface property gradient, a capillary flow, or any combination thereof. It is contemplated that translocating includes controllably moving at least a portion of the macromolecule into at least a portion of a fluidic nanochannel segment; moving at least a portion of the macromolecule through at least a portion of a fluidic nanochannel segment at a controlled speed and a controlled direction.

Monitoring includes displaying, analyzing, plotting, or any combination thereof. Ways of monitoring signals will be apparent to those of ordinary skill in the art.

The one or more monitored signals include optical signals, a radiative signals, fluorescent signals, electrical signals, magnetic signals, chemical signals, or any combination thereof.

Signals are, in certain embodiments, generated by an electron spin resonance molecule, a fluorescent molecule, a chemiluminescent molecule, a radioisotope, an enzyme substrate, a biotin molecule, an avidin molecule, an electrical charged transferring molecule, a semiconductor nanocrystal, a semiconductor nanoparticle, a colloid gold nanocrystal, a ligand, a microbead, a magnetic bead, a paramagnetic particle, a quantum dot, a chromogenic substrate, an affinity molecule, a protein, a peptide, a nucleic acid, a carbohydrate, an antigen, a hapten, an antibody, an antibody fragment, a lipid, or any combination thereof.

In some embodiments, the molecule is unlabeled and monitored by infrared spectroscopy, ultraviolet spectroscopy, or any combination thereof.

The signal is generated by using one or more excitation sources to induce fluorescence, chemoluminescence, phosphorescence, bioluminescence, or any combination thereof. Suitable excitation sources include lasers, visible light sources, sources of infrared light, sources of ultraviolet light, or any combination thereof.

Correlating comprises determining the features of a distinct macromolecule or a portion thereof from a population of macromolecules by partial or full elongation of the macromolecule in a fluidic nanochannel segment. In some embodiments, at least a portion of the macromolecule is stationary during the monitoring.

It is contemplated that in some cases, at least a portion of the macromolecule is translocated within at least a portion of the fluidic nanochannel segment more than one time. Such translocation allows for multiple analyses of the same region of a given macromolecule.

Correlating suitably includes determining the length of at least a portion of the macromolecule, determining the apparent partially elongated length of at least a portion of the macromolecule as confined within one or more fluidic nanochannel segments. The apparent partially elongated length is determined as the linear distance along the fluidic nanochannel segment within which a partially elongated macromolecule is confined.

It is contemplated that correlating also includes determining the identity of one or more components of the macromolecule or determining the sequence of one or more components of the macromolecule, or determining the presence of one or more modifications to at least a portion of the macromolecule, or any combination thereof.

Correlating is performed by automated means, computerized means, mechanical means, manual means, or any combination thereof. Correlating includes one or more algorithms for characterizing a duplex nucleic acid molecule based on observed signal modulations through the detection region of a nanochannel, wherein said algorithm is present on a computer readable medium.

It is contemplated that he one or more characteristics of the macromolecule are one or more target features present on at least a portion of the macromolecule. Suitable target features include epigenetic factors, such as methylation patterns.

Target features also include one or more genomic structures, including the position of one or more particular molecular sequences, SNPs, haplotypes, repetitive elements, copy numbers polymorphisms, a change in one or more loci on a DNA molecule, open reading frames, introns, exons, regulatory elements, or any combination thereof. Target features also include compound/drug binding sites/complex, DNA repairing or cleaving binding sites/complex, SiRNA or anti-sense nucleotides binding sites/complex, transcription/regulatory factor binding sites/complex, restriction enzyme binding/cleaving sites/complex, or any other genetically engineered or chemically modified binding sites/complexes, or any combination thereof.

The present methods can, in some embodiments, further include contacting a macromolecule with a first labeled probe of known length L1, wherein the first labeled probe is complementary to a control genomic sequence whose copy number is known, and with a second labeled probe of known length L2, wherein the second labeled probe is specific to a nucleotide sequence of interest; introducing the macromolecule into at least a portion of the fluidic nanochannel segment; elongating the labeled macromolecule within the fluidic nanochannel segment; detecting binding between the first labeled probe and the genomic control sequence and between the second labeled probe and the nucleotide sequence of interest; and ascertaining the total length of the hybridization signals that correspond to the binding of the first labeled probe (S1) and the second labeled probe (S2).

The present methods further include calculating the copy number of the nucleotide sequence of interest. The the copy number is calculated by calculating the ratios N1=S1/L1 and N2=S2/L2, wherein N1 corresponds to the copy number of the genomic control sequence and N2 corresponds to the copy number of the nucleotide sequence of interest. It is contemplated that the copy number of the control sequence is an integer, and that the difference between N2 and N1 indicates an abnormality in the genome being analyzed.

The methods further contemplate that the control genomic sequence includes separate portions whose total length per genome is known, wherein the sequence of interest comprises separate portions whose length per normal gene is known, and wherein a significant difference between N2 and N1 indicates a genetic abnormality in the genome.

In some embodiments, the nucleotide sequence of interest can relate to a trisomy-linked chromosome, wherein the control genomic sequence is from a chromosome other than the trisomy-linked chromosome, and wherein a N2/N1 ratio of approximately 1.5 indicates a trisomic genotype. In other embodiments, the nucleotide sequence of interest comprises a deletion of a portion of a genome. In still other embodiments, the nucleotide sequence of interest comprises a repeating sequence.

In some aspects, the present method includes embodiments wherein the control genomic sequence and the nucleotide sequence of interest are identical for a given genome, and wherein one or more different genomes are analyzed within one or more fluidic nanochannel segments so as to determine the respective quantities of each genome present.

It is contemplated that the N2/N1 ratio has a statistical error of less than 20%.

It is further contemplated that the methods include embodiments where the control genomic sequence and nucleotide sequence of interest are from the same genome, or even where the control genomic sequence is from the same chromosome as the nucleotide sequence of interest.

The instant methods can further include so-called flanked probes, labeling regions of a sample nucleotide at either end of a nucleotide zone of interest and regions of a control nucleotide at either end of a nucleotide zone of interest. In such embodiments, the methods include (a) introducing the labeled nucleotides into separate fluidic nanochannel segments having a cross-sectional diameters sufficient to at least substantially elongate the labeled nucleotides, (b) determining the distance between the labels on the sample nucleotide and the control nucleotide, respectively, and repeating steps (a) and (b) one or more times so as to further linearize the sample and control nucleotides and so as to obtain additional information regarding the distance between the labels on the control and sample nucleotides as the nucleotides elongate.

These embodiments further include determining the length of the zone of interest on the sample nucleotide by comparing the distance between the labels on the control and sample nucleotides, wherein a difference between the distance between the labels on the control and sample nucleotides indicates an abnormality in the zone of interest on the sample nucleotide.

Further provided are devices, comprising: a substrate comprising a surface and one or more fluidic nanochannel segments disposed substantially parallel to the surface, wherein at least one of the fluidic nanochannel segments is capable of containing and elongating at least a portion of a macromolecule residing within at least a portion of the fluidic nanochannel segment, and wherein each of the fluidic nanochannel segments has a characteristic cross-sectional dimension of less than about 1000 nm and a length of at least about 10 nm; and wherein at least a portion of at least one fluidic nanochannel segment is illuminated by one or more excitation sources.

Suitable fluidic nanochannel segments and patterns and dimensions thereof are described elsewhere herein. Suitable substrates are also described elsewhere herein.

It is contemplated that the present devices include, in some embodiments, a viewing window disposed between the illuminated fluidic nanochannel segment and the illumination source, wherein the viewing window comprises a slit, and, in some embodiments, is removable. It is also contemplated that the viewing window is capable of placing the contents of one or more fluidic nanochannel segments into fluid communication with the environment external to the fluidic nanochannel segment.

Nanochannel segments are characterized as trenches, which trenches are described elsewhere herein. Caps suitable for covering such trenches are also described elsewhere herein, and it is contemplated that one or more macromolecules are at least partially elongated in the fluidic nanochannel segment, and remain in a substantially elongated form after the cap is removed.

Fluidic nanochannels are also characterized as a zone bordered by one or more regions having a surface chemistry, which fluidic nanochannels are described elsewhere herein.

One or more fluidic nanochannel segments is in fluid communication with one or more suitable fluidic devices, which are described elsewhere herein, and include a screen, an occlusion, a gel, a heater, a splitter, a reservoir, or any combination thereof.

In some embodiments, the devices include one or more obstacles situated in proximity to one or more nanochannels. Such obstacles may assist in unfolding or unraveling macromolecules to enhance the ability of a macromolecule to enter into the nanochannel.

Macromolecules suitable for use in the present invention are described elsewhere herein. As described elsewhere, the devices may include comprising one or more connectors capable of placing the device in fluid communication with one or more apparatuses external to the device. Suitable apparatuses are described elsewhere herein.

Excitation sources suitable for use in the device include lasers, halogen lights, mercury lamps, sources of infrared light, source of ultraviolet light, diodes, waveguides, radioactive sources, or any combination thereof. Devices can further include one or more filters capable of transmitting a spectrum of excitation source light.

The portion of the at least one illuminated fluidic nanochannel segment illuminated by one or more excitation sources is characterized as being one or more slits, as one or more circular spots, ovals, polygons, or any combination thereof.

Suitable excitation sources are capable of being scanned across at least a portion of at least one fluidic nanochannel segment. In some embodiments, the device includes one or more excitation sources.

Devices suitably include a detector disposed so as to be capable of receiving an optical signal originating from within one or more illuminated fluidic nanochannel segments.

Suitable detectors include a charge coupled device (CCD) detection system, a complementary metal-oxide semiconductor (CMOS) detection system, a photodiode detection system, a photo-multiplying tube detection system, a scintillation detection system, a photon counting detection system, an electron spin resonance detection system, a fluorescent detection system, a photon detection system, an electrical detection system, a photographic film detection system, a chemiluminescent detection system, an enzyme detection system, an atomic force microscopy (AFM) detection system, a scanning tunneling microscopy (STM) detection system, a scanning electron microscopy (SEM) detection system, an optical detection system, a nuclear magnetic resonance (NMR) detection system, a near field detection system, a total internal reflection (TIR) detection system, a patch clamp detection system, a capacitive detection system, or any combination thereof.

Also disclosed are macromolecular analysis devices. The disclosed devices include one or more nanochannels disposed on a surface, with one or more of the nanochannels having a width of less than about 1000 nm, and one or more of the nanochannels being defined by one or more borders and being capable of constraining at least a portion of the macromolecule so as to maintain in linear form that portion of the macromolecule.

Nanochannels suitably have a length in the range of from about 10 nm to about 10 cm, or from about 100 nm to about 1 cm. While nanochannels may be straight, parallel, interconnected, curved, or bent, nanochannels of the instant invention suitably include at least one essentially straight portion in the length of from about 10 nm to ab out 100 cm, or in the range of from about 100 nm to about 10 cm, or even from about 1 mm to about 1 cm. As an example, the claimed invention includes embodiments wherein nanochannels arranged in a back-and-forth, radiator-type pattern on a surface.

The width of nanochannels is suitably less than 1000 nm, or less than 500 nm, or less than 50 nm. In some embodiments, the nanochannels suitably have a width of less than about 10 nm, or even less than about 5 nm.

As discussed, two or more nanochannels according to the present invention may be interconnected. A nanochannel may have a constant cross-section or may vary in cross-section, depending on the user's needs.

Borders that define the nanochannels of the present invention have various configurations. A border may suitably be a physical wall, a ridge, or the like. Alternatively, a border includes an electrically charged region, a chemically-treated region, a region of magnetic field, and the like. Hydrophobic and hydrophilic regions are considered especially suitable borders. In some cases, borders are formed from differing materials—e.g., strips of glass, plastic, polymer, or metal. In other embodiments, borders are formed by self-assembling monolayers (SAMs). In other embodiments, the nanochannels are of an inverse construction wherein exposed surface defines the borders of the nanochannel, and the central lane of the channel is qualitatively different from the exposed bordering surface. Nanochannels are suitably capable of confining at least a portion of a macromolecule so as to elongate or unfold that portion of the macromolecule. For example, a macromolecule that is hydrophilic may be elongated by placement or disposition within a nanochannel bounded by hydrophobic borders. In this example, the macromolecule will be constrained by the borders and will become elongated.

Surfaces suitable for the disclosed devices include glass, ceramics, silicon, metals, polymers, and the like. Surfaces will be chosen according to the user's needs, and as will be apparent to those of ordinary skill in the art, certain surfaces will be optimally amendable to various chemical or other treatments needed to define border regions on such surfaces.

The claimed devices also include a viewing window disposed above at least a portion of at least one nanochannel. Such viewing windows may be permeable to one or more macromolecules. As an example, a viewing window may include one or more pores, holes, channels, or nanochannels, any of which will enable macromolecules to move in three dimensions in the claimed devices. Such three-dimensional configurations permit introduction and routing of macromolecules in a number of directions and, in some embodiments, enable simultaneous viewing of multiple regions of macromolecules within the claimed devices.

The disclosed inventions also include detectors. Such detectors are suitably able to monitor or capture a signal evolved from a molecule within the claimed devices; which detectors include CCD cameras or photon-counter devices.

The claimed inventions also provide methods of analyzing macromolecules. The methods include disposing one or more macromolecules onto a surface having one or more nanochannels capable of constraining at least a portion of the macromolecule so as to maintain in linear form that portion of the macromolecule, subjecting the one or more macromolecules to a motivating force so as to elongate at least a portion of one or more macromolecules within one or more nanochannels, and monitoring one or more signals evolved from one or more of the macromolecules.

Macromolecules are suitably disposed onto a surface by comprises dispensing, dropping, flowing, and the like. Macromolecules are suitably carried in a fluid, such as water, a buffer, and the like, to aid their disposition onto the surfaces. The carrier fluid is chosen according to the needs of the user, and suitable carrier fluids will be known to those of ordinary skill in the art.

In some embodiments, one or more macromolecules are disposed at least partially within one or more nanochannels.

Suitable motivating forces include pressure gradients, magnetic fields, electric fields, receding menisci, surface tension forces, thermal gradients, pulling forces, pushing forces, and the like. Other manners of applying a force to macromolecules will be known to those of ordinary skill in the art, which manners include optical traps, optical tweezers, physical probes, atomic force microscopes, and the like. Motivating forces may be constant, variable, alienating, and the frequency and intensity of a motivating force will depend on the user's needs.

In some embodiments, one or more macromolecules is tethered to the surface for analysis. Tethering may be accomplished by biotin-avidin bonds, by interactions between gold and thio-groups, and by antibody-antigen or antibody-epitope interactions. Users of ordinary skill in the art will be aware of suitable ways to tether molecules to surfaces.

In other embodiments, a macromolecule is at least partially immobilized by a dynamic force. For example, a macromolecule may include a bead at one end, which bead is larger in diameter than the cross-section of a particular nanochannel. Application of fluid flow to such a macromolecule will result in the macromolecule's bead being stuck at one end of the nanochannel so as to immobilize the macromolecule extending into at least a portion of the nanochannel. In such embodiments, the macromolecule may be released from the nanochannel by application of an opposing motivating force, e.g., by reversing the direction of the fluid flow field. Magnetic and electric fields are also suitably used to immobilize macromolecules in nanochannels, which field are easily reversed to free such immobilized macromolecules. In such a way, a given set of nanochannels may be re-used to analyze a given macromolecule multiple times or be recycles to analyze a different macromolecule or sets of macromolecules.

Monitoring a signal evolved from a macromolecule is accomplished by, inter alia, recording, plotting, or displaying the signal; monitored signals are suitably derived from a portion of a macromolecule that is in substantially linear form within a nanochannel. The monitoring may be performed through a viewing window or by directly interrogating one or more macromolecules.

The disclosed methods also include analyzing one or more evolved signals, which analysis suitably includes correlating one or more monitored signals to one or more characteristics of one or more macromolecules. Correlating could include, for example, relating the existence of a particular signal to the existence of a particular mutation on a segment of DNA.

Also provided are methods of fabricating a macromolecular analysis devices. These methods include defining one or more nanochannels on a surface by disposition of two or more borders, where one or more of the borders being capable of constraining a macromolecule, and one or more of the nanochannels has a width of less than about 1000 nm.

Nanochannels formed by the instant methods may have widths of less than 500 nm, less than 100 nm, less than 50 nm, or even less than 10 nm. The optimal width of a nanochannel will be dictated by the needs of the user and by the macromolecules under study.

Disposition of borders is accomplished by, inter alia, rendering electrically charged at least a portion of the surface, rendering at least a portion of the surface hydrophobic, rendering at least a portion of the surface hydrophilic, rendering at least a portion of the surface magnetic, or any combination thereof. In one embodiment, disposition of is accomplished by contacting at least a portion of the surface with a mold having a surface profile that comprises a surface profile that is complementary to the desired pattern of borders or nanochannels. Molds suitable for the present invention comprise one or more nanoscale features, and may be fabricated by methods known to those skilled in the art.

Figure 7:
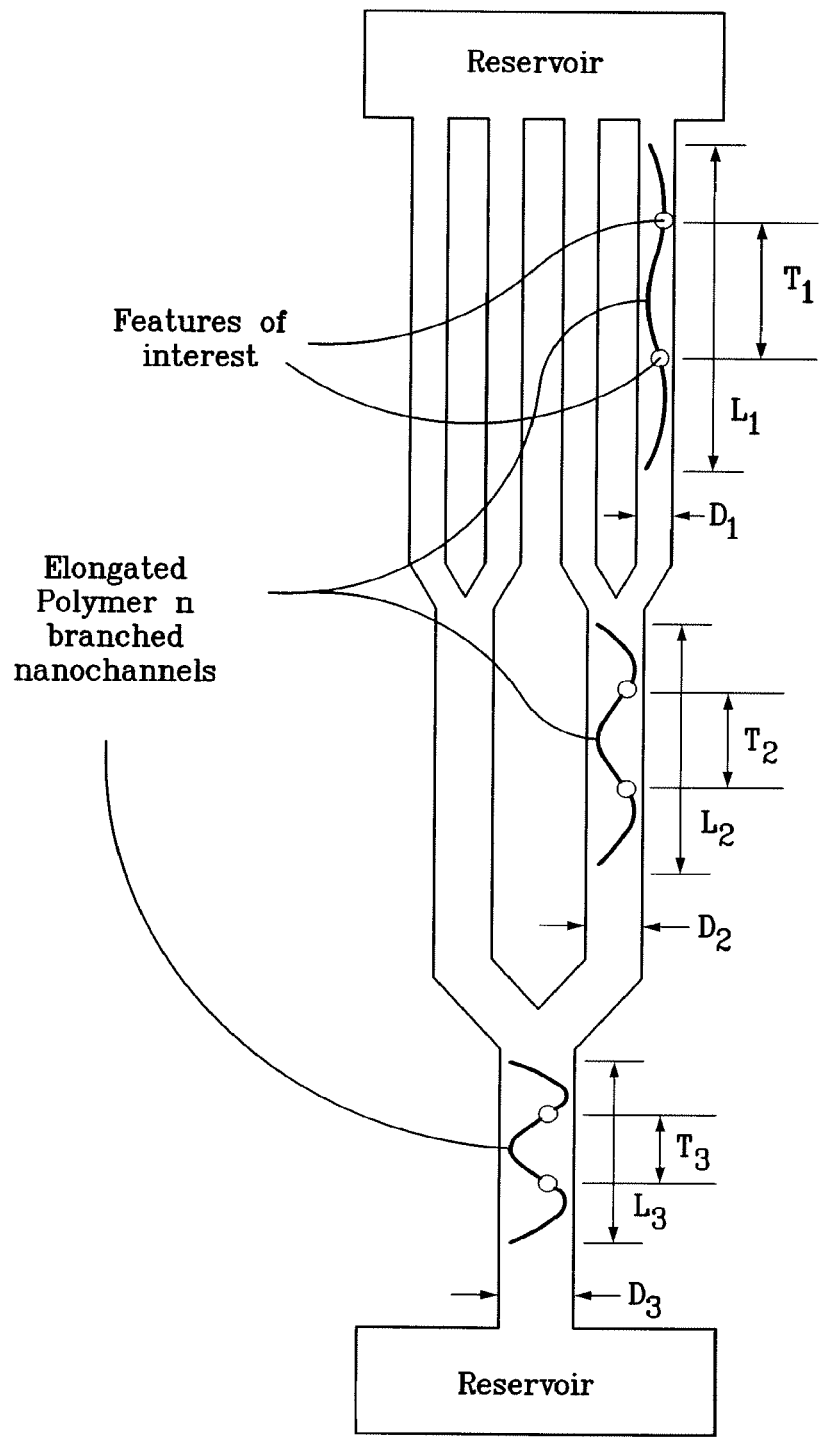
FIG. 7 illustrates a branched nanochannel network in which each nanochannel is connected to one or more nanochannels—as the macromolecule flows through the network, the macromolecule's degree of elongation is a function of the cross-sectional dimension of the nanochannel, and for an example macromolecule flowing through three successive nanochannels whereby their cross-sectional diameters varies (D3>D2>D1), the macromolecule's degree of elongation will also vary (L3<L2<L1), similarly the distance between features of interest on the macromolecule will vary in a scalable manner (T3<T2<T1)
Figure 8A:
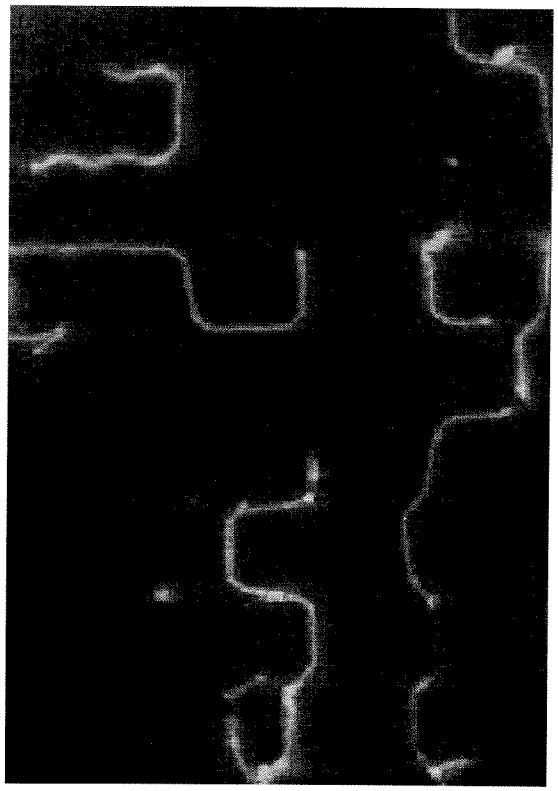
FIG. 8A is an illustration of labeled macromolecules traversing a number of fluidic nanochannel segments, where the segments are disposed in a grid-like pattern, and where the DNA molecules are elongated as they traverse the segments
Figure 8B:
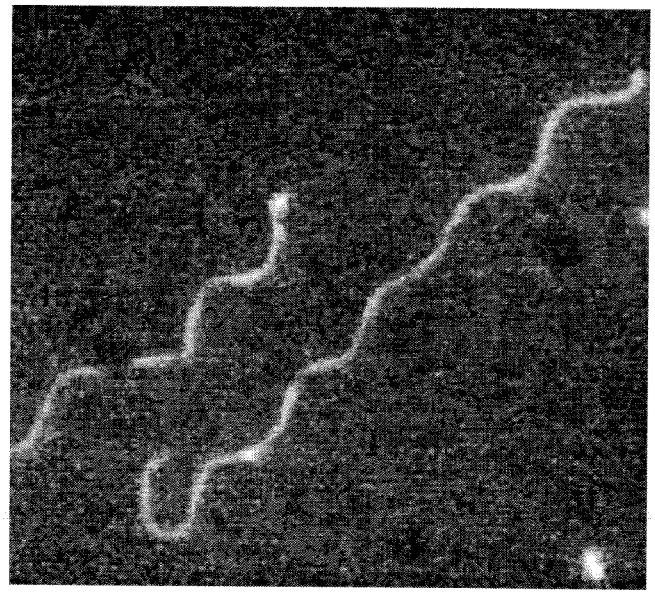
—FIG. 8B depicts labeled macromolecules traversing non-linear fluidic nanochannel segments.

One exemplary embodiment is shown in FIG. 9B, which figure illustrates nanochannels or nanolanes defined by borders of Surface B—which may be a hydrophobic surface—and lanes of Surface A, which surface may be hydrophilic or other surface different from Surface B. Similar borders may also be used to define more intricate patterns of nanochannels, such as those shown in FIG. 7.

Figure 17:
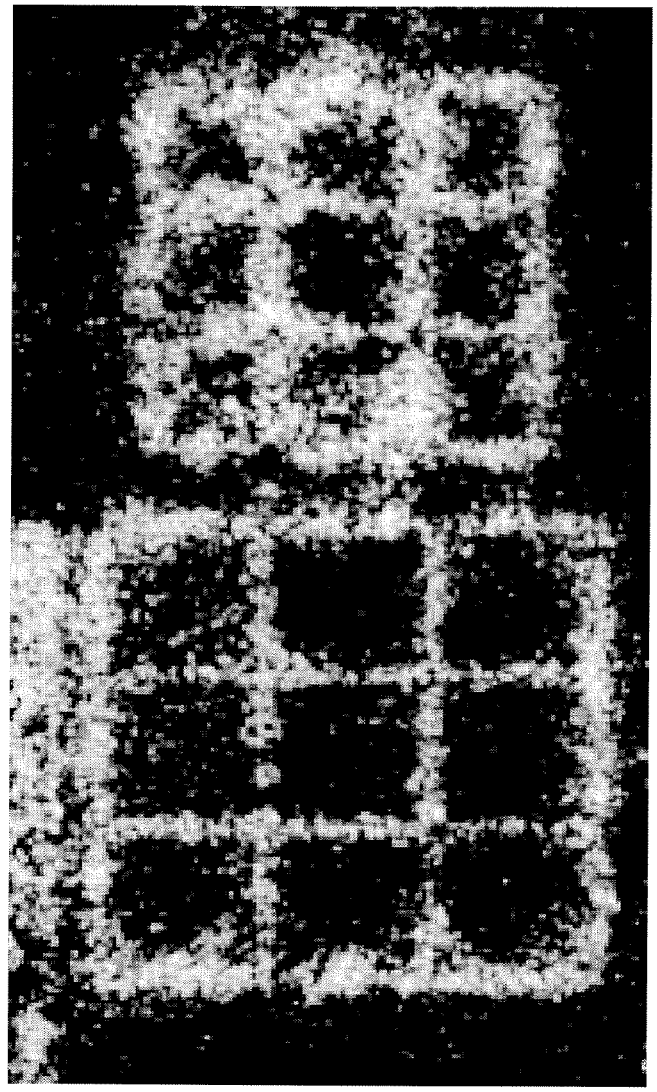
FIGS. 17 and 18 are micrographs of patterns formed on a surface having charged and uncharged regions; the charged regions are marked with indicator dust.
Figure 18:
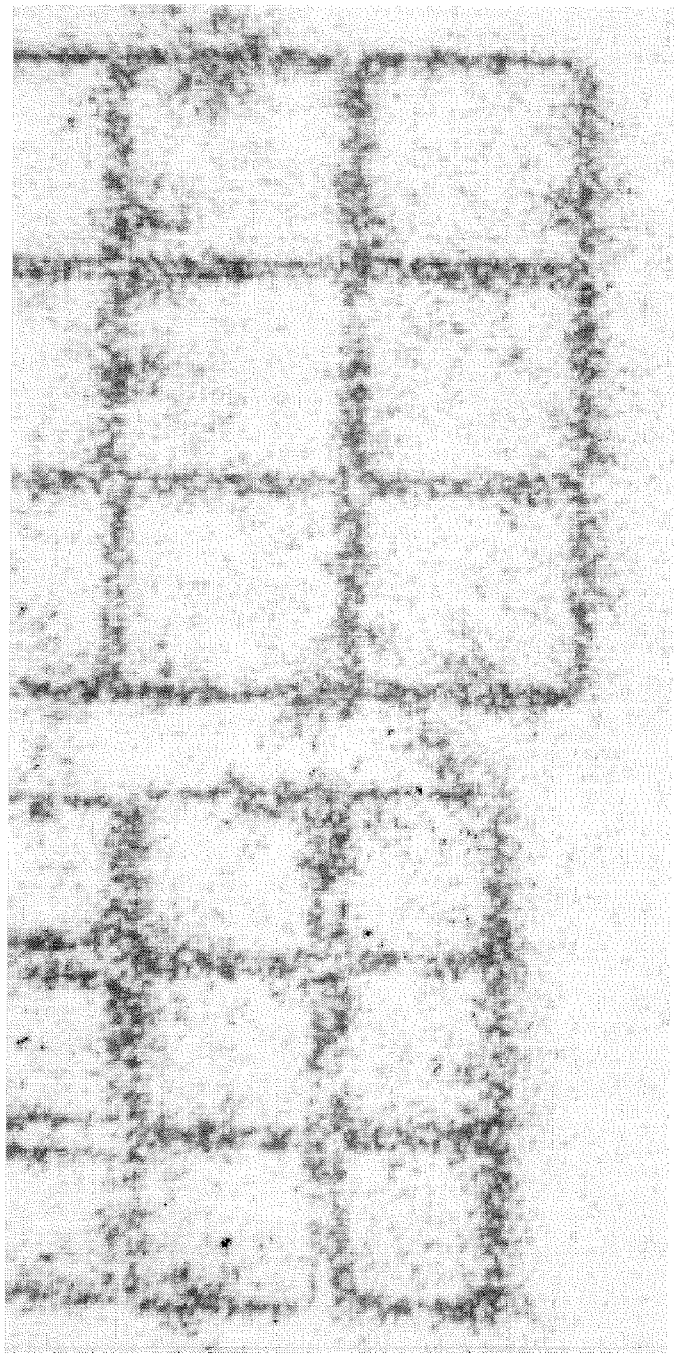
Figure 19:
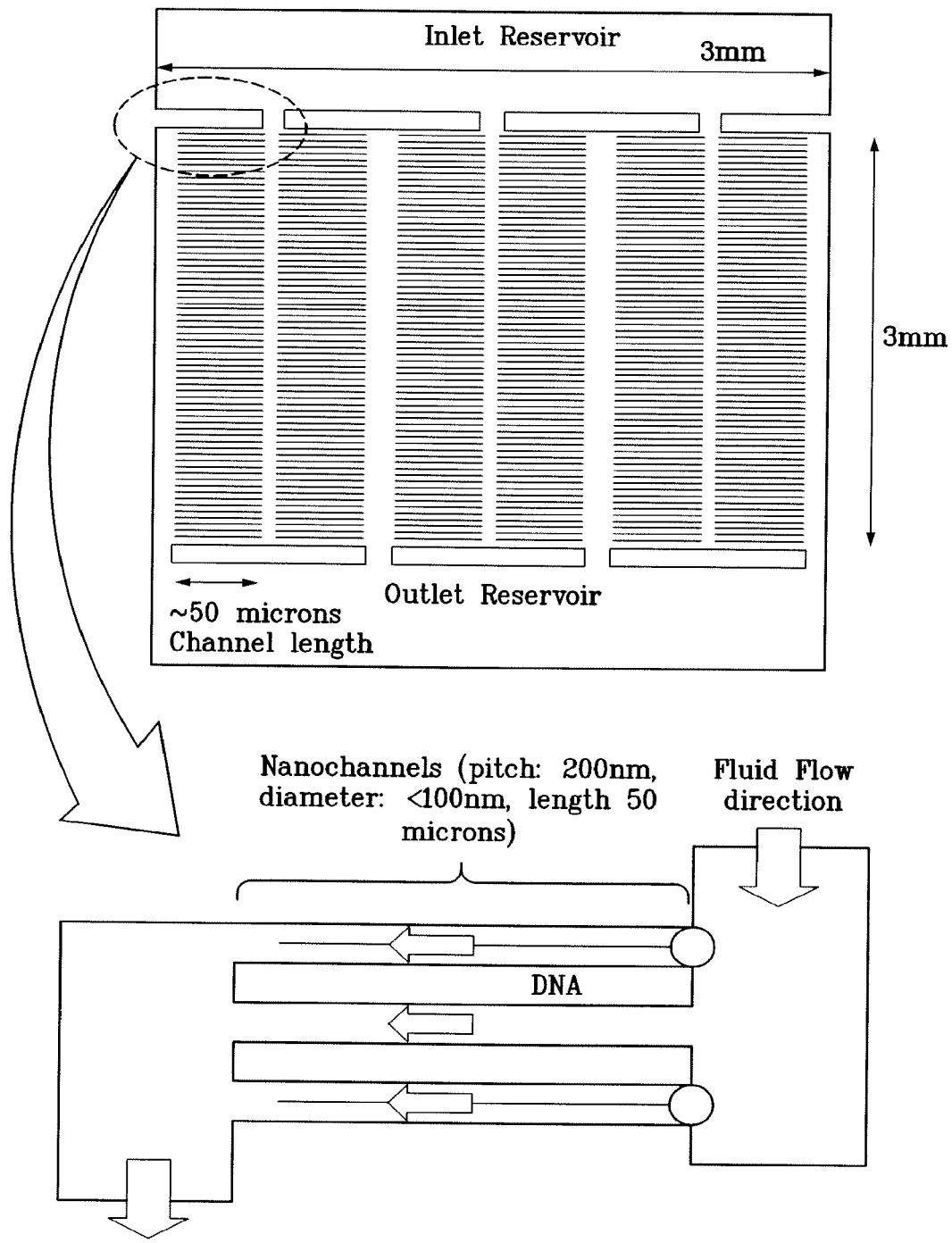
FIG. 19 depicts a nanochannel array wherein macromolecules include beads that act to immobilize the macromolecules at the inlet or entry of the macromolecules—the beads are sized to obstruct the inlets of the nanochannels.

For example, a mold or other substrate comprising nanochannels can be contacted with a hydrophobic compound. The mold is then contacted with a hydrophilic surface, leaving behind hydrophobic patches on the surface that act as borders, defining nanochannels on the surface that corresponds to the nanochannel pattern on the mold. Molds or other patterns may also be used to effect regions of electric charge or of magnetic fields. This is accomplished by, inter alia, contacting the mold with a charge-carrying species, a hydrophobic species, a hydrophilic species, a magnetic species, a ferromagnetic species, or any combination thereof. Exemplary patterns are shown in FIGS. 17 and 18, which patterns were produced by disposing regions of charge on substrates and highlighting those regions of charge by spreading an indicator dust over the substrates that bound to the charged regions and removing the unbound dust.

EXAMPLES AND OTHER ILLUSTRATIVE EMBODIMENTS

General Procedures.

Deposition of capping material was provided by sputtering, CVD, e-beam evaporation with a tilted sample wafer at various angles. This step was used to both reduce the nanochannel diameter and provide a cap.

In most cases, 100-340 nm of $SiO_2$ was deposited onto the channel openings. Effective sealing was achieved with various deposition conditions that were tested. At gas pressure of 30 mTorr, RF power of ~900 W, and DC bias of 1400 V, a deposition rate of ~9 nm/min was achieved. At lower pressure of 5 mTorr, the deposition rate was increased to an estimated 17 nm/min. Filling material was deposited on the nanochannel opening by sputtering at 5 mTorr. Further details about making nanochannel arrays and devices can be found in U.S. Patent Application Pub. Nos. VS 2004-0033515 A1 and VS 2004-0197843 A1, the entirety of each is incorporated by reference herein.

Example 1

A silicon substrate having a plurality of parallel linear channels that had an 100 nm trench width and a 100 nm trench height was provided. These channel openings were sputtered at a gas pressure of 5 mTorr according to the general procedures given above. The sputter deposition time was 10-25 minutes to provide a nanochannel array that can range from not completely sealed to completely sealed. Silicon dioxide was deposited by an e-beam (thermo) evaporator (Temescal BID-1800) onto the substrate. The substrate was placed at various angles incident to the depositing beam from the silicon dioxide source target; the deposition rate can be set to about 3 nm/minute and 150 nm of sealing material was deposited in about 50 minutes. The angle of the incident depositing beam of sealing material could be varied to reduce the channel width and height to less than 150 nm and 150 nm, respectively, and to substantially sealed by providing shallow tangential deposition angles.

Example 2

In this example, a nanochannel array was contacted with a surface-modifying agent. A nanochannel array made according to Example 1 can be submerged in a surface-modifying agents solutions containing polyethelyene glycol inside a vacuum chamber to facilitate wetting and treatment of the channels and degas the air bubbles that might be trapped inside the nanochannels.

Example 3

This example describes how to provide a sample reservoir with a nanochannel array to provide a nanofluidic chip. A nanochannel array having 100 nm wide, 100 nm deep nanochannels was made according to general procedures of Example 1. The nanochannel array was spin-coated with a photoresist and imaged with a photomask to provide regions on opposite ends of the channel array. The exposed areas were etched using reactive ion etching to expose the nanochannel ends and to provide a micron-deep reservoir about a millimeter wide on the opposite ends of the channels at the edge of the substrate.

Example 4

This example describes how to fill a nanofluidic chip with a fluid containing DNA macromolecules to analyze the DNA. A cylindrical-shaped plastic sample-delivery tube of 2 mm diameter was placed in fluid communication with one of the reservoirs of the nanochannel array of Example 3. The delivery tube was connected to an external sample delivery/collection device, which can be in turn connected to a pressure/vacuum generating apparatus. The nanochannels were wetted using capillary action with a buffer solution. A buffer solution containing stained for example lambda phage macromolecules (lambda DNA) were introduced into the nanochannel array by electric field (at 1-50 V/cm); the solution concentration was 0.05-5 microgram/mL and the lambda DNA was stained at a ratio of 10:1 base pair/dye with the dye TOTO-1 (Molecular Probes, Eugene, Oreg.). This solution of stained DNA was diluted to 0.01-0.05 microgram/mL into 0.5×TBE (tris-boroacetate buffer at pH 7.0) containing 0.1M of an anti-oxidant and 0.1% of a linear polyacrylamide used as an anti-sticking agent.

Example 5

This example describes how to image DNA whole or substantial parts of macromolecules linearized within nanochannels. The DNA macromolecules were fluorescently labeled and flowed into the nanochannels according to the procedures discussed in Example 4. An excitation light source such as a 100W halogen lamp was focused through a 60X lens onto the nanochannels thereby exciting DNA molecules within the field of view. Fluorescent light emission from the TOTO-1 dye molecules is collected through the lens, was reflected by a dichroic filter and passed through a filter that allows transmission of the wavelength band emitted by TOTO-1. The light was detected using a CCD camera thus producing an image of the DNA molecules in the field of view.

Example 6

This example describes how to detect DNA macromolecules as they pass through a detection area that is smaller than the end-to-end physical length of DNA molecules linearized within nanochannels. DNA was stained and flowed into the nanochannels as described in Example 4. The detection area was constrained by defining a narrow slit through which excitation light can pass. The slit was defined using a 100 nm film of aluminum deposited on top of the nanochannels and then opening a 1 micron slit in the aluminum using photolithography and chlorine plasma etching. As the DNA passed through the part of the nanochannel under the aluminum slit, it was exposed to the excitation light and emits fluorescent light. The fluorescent emission was collected as described in Example 5 but detected using a photomultiplier tube (PMT). The PMT registered a signal until the DNA molecule completely passed by the slit. By correlating the speed at which DNA moves past the slit (typically 1-100 microns/sec) to the length of time that a signal is detected, the size of the DNA molecule is determined.

What is claimed is:

1. A method of detecting a copy number abnormality in a genome of interest, the method comprising:
    obtaining a first sample comprising one or more isolated nucleic acid molecules of the genome of interest;
    labeling one or more regions, including at least a first region, of the isolated nucleic acid molecules of the genome of interest;
    translocating at least a portion of at least the first region of each of the labeled isolated nucleic acid molecules through a fluidic nanochannel segment disposed substantially parallel to a substrate surface, wherein the fluidic nanochannel segment is capable of containing and elongating at least a portion of the region of the nucleic acid, and wherein the fluidic nanochannel segment has a characteristic cross-sectional dimension of less than about 1000 nm and a length of at least about 10 nm, wherein said translocating comprises introducing the labeled isolated nucleic acid molecules into separate fluidic nannochannel segments each having a cross-sectional diameter of less than about 200 nm so as to at least substantially linearize at least a part of the labeled nucleic acid molecules;
    during said translocating, capturing through a viewing window a total length of time that signals corresponding to each first region of the labeled individual isolated nucleic acid molecules of the genome of interest are detected through the viewing window, said total length of time correlating to the speed at which said labeled isolated nucleic acid molecules move through the fluidic nanochannel segment, thereby ascertaining a length of nucleic acids corresponding to the first region; and
    comparing the total length of time of signals of each first region of the labeled individual isolated nucleic acid molecules of the genome of interest to a total length of time of signals of a control, whereby a copy number of at least the first region of the isolated nucleic acid molecules of the genome of interest is ascertained from the comparing of lengths of time.

2. The method of claim 1, wherein the control comprises a second region of the genome of interest.

3. The method of claim 2, further comprising ascertaining a copy number of the second region of the control, and then comparing the copy numbers of the first region and the second region.

4. The method of claim 3, wherein the first region is a trisomy-linked region and the second region of the control is different from the trisomy-linked region.

5. The method of claim 4, wherein labeling comprises binding a first label to a trisomy-linked chromosome comprising the trisomy-linked region of the first region and binding a second label to the second region of the control, wherein the second region of the control is on a chromosome other than the trisomy-linked chromosome.

6. The method of claim 5, wherein comparing the total length of time of signals of each first region of the labeled isolated nucleic acid molecules of the genome of interest to the total length of time of signals of the control comprises calculating a ratio of the total length of time of signals from each first region to the total length of time of signals from the second region of the control, wherein the ratio varies with copy number of the respective first and second regions.

7. The method of claim 6, wherein a ratio of about 1.5:1 is indicative of trisomy in the sample of interest.

8. The method of claim 1, wherein the copy number abnormality comprises a trisomy.

9. The method of claim 1, wherein labeling one or more regions, including at least the first region, of the isolated nucleic acid molecules of the genome of interest comprises:
    contacting the isolated nucleic acid molecules of the genome of interest with:
    a first labeled probe of known length L1, wherein the first labeled probe is complementary to a genomic sequence of the control, wherein the copy number of the control is known; and
    a second labeled probe of known length L2, wherein the second labeled probe is specific to the first region;
    detecting binding between the first labeled probe and the genomic sequence of the control and between the second labeled probe and the first region; and
    ascertaining the total length of the hybridization signals that correspond to the first labeled probe (S1) and the second labeled probe (S2),
    wherein the copy number of at least the first region is calculated by calculating the ratios $N1=S1/L1$ and $N2=S2/L2$, wherein N1 corresponds to the copy number of the genomic sequence of the control and N2 corresponds to the copy number of the first region.

10. The method of claim 1, wherein capturing a total length of time that signals corresponding to each first region are detected through the viewing window further comprises identifying a haplotype of the genome of interest.

11. The method of claim 1, wherein the total length of time of signals of the control comprises information from a different genome than the genome of interest.

12. The method of claim 1, wherein labeling one or more regions, including the first region, of the one or more isolated nucleic acid molecules of the genome of interest comprises contacting the isolated nucleic acid molecules with a first label of a known length, wherein the first label is specific to the first region, and;

and wherein ascertaining the copy number of at least the first region of the isolated nucleic acid molecules comprises determining a first ratio of the total length of time of signals of each first region to the known length of the first label, so that the first ratio corresponds to a copy number of at least the first region of the isolated nucleic acid molecules.

13. The method of claim 12, further comprising comparing the first ratio to a second ratio, wherein the second ratio corresponds to a copy number of a sequence of the control having a known length and a known copy number, and wherein a difference between the first ratio and the second ratio indicates a copy number abnormality of nucleic acids corresponding to the first region.

14. The method of claim 13, further comprising: contacting the isolated nucleic acid molecules with a second label of known length, wherein the second label is specific to the sequence of the control.

15. The method of claim 13, wherein the second ratio comprises labeling pattern information from a different genome than the genome of interest.

16. The method of claim 13, wherein the sequence of the control is the same as the sequence of the first region, and the second ratio comprises labeling pattern information from a different genome than the genome of interest.

17. The method of claim 12, wherein the first region comprises a repeating sequence.

18. The method of claim 1, wherein the first region comprises separate portions whose length per normal genome is known.

19. The method of claim 1, wherein the control comprises separate portions whose total length per normal genome is known.

20. The method of claim 1, wherein labeling comprises labeling with at least one of a fluorescent label, a magnetic label, or a radioactive label.

21. The method of claim 1, wherein the labeled isolated nucleic acid molecules are from a single cell.

22. The method of claim 1, further comprising ascertaining, based on total length of time of the signals, a copy number of at least the first region on a single isolated nucleic acid molecule of the genome of interest.

23. The method of claim 1, wherein the control comprises a nucleotide sequence from a different genome than the genome of interest.

24. The method of claim 1, wherein the viewing window comprises a slit, a porthole, a square, or any combination thereof.

25. The method of claim 1, wherein the viewing window is capable of permitting optical inspection of at least a portion of the contents of the fluidic nanochannel segment.

26. The method of claim 1, wherein the viewing window is capable of permitting optical inspection of all of the contents of the fluidic nanochannel segment.

27. The method of claim 1, wherein the viewing window is removable.

* * * * *